(12) United States Patent
Lin et al.

(10) Patent No.: US 6,635,670 B2
(45) Date of Patent: Oct. 21, 2003

(54) SPLA$_2$ INHIBITORS

(75) Inventors: Ho-Shen Lin, Indianapolis, IN (US); Michael Enrico Richett, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/260,450

(22) Filed: Sep. 27, 2002

(65) Prior Publication Data

US 2003/0153770 A1 Aug. 14, 2003

Related U.S. Application Data

(62) Division of application No. 10/018,037, filed as application No. PCT/US00/16319 on Jul. 11, 2000.
(60) Provisional application No. 60/144,502, filed on Jul. 19, 1999.

(51) Int. Cl.[7] .................. A61K 31/404; C07D 209/20
(52) U.S. Cl. ........................ 514/419; 548/493
(58) Field of Search .................. 514/397, 419, 514/422; 548/312.1, 467, 493

(56) References Cited

U.S. PATENT DOCUMENTS 5,684,034 A    11/1997   Nicholas et al.

FOREIGN PATENT DOCUMENTS

| EP | 0 620 215 | 10/1994 |
| EP | 0 675 110 | 10/1995 |
| EP | 0 952 149 | 10/1999 |
| WO | WO 91 06537 | 5/1991 |
| WO | WO 96 37469 | 11/1996 |
| WO | WO 99 21546 | 5/1999 |
| WO | WO 99 21559 | 5/1999 |
| WO | WO 00 37358 | 6/2000 |

OTHER PUBLICATIONS

STN International R CAPLUS Database, Accession No. 1996:713060; Draheim et al. Journal of Medicinal Chemistry 39(26), 5159–5175 (1996), abstract, compound RN 185298–58–2.*

Dillard, R. D., et al., vol. 39, No. 26, "Indole Inhibitors of Human Nonpancreatic Secretory Phospholipase A21. Indole–3–Acetamides," *Journal of Medicinal Chemistry*, US, American Chemical Society. Washington. pp. 5119–5136 (1996); XP002046054.

* cited by examiner

*Primary Examiner*—Joseph K. McKane
*Assistant Examiner*—Sonya Wright
(74) *Attorney, Agent, or Firm*—Francis O. Ginah

(57) ABSTRACT

A class of novel indole is disclosed together with the use of such compounds for inhibiting sPLA$_2$ mediated release of fatty acids for treatment of Inflammatory Diseases such as septic shock.

6 Claims, No Drawings

SPLA₂ INHIBITORS

This application is a DIV of 10/018,037 filed Dec. 11, 2001, which is a 371 of PCT/US00/16319 filed Jul. 11, 2000, which claims benefit of 60,144,502, filed Jul. 19, 2000.

FIELD OF THE INVENTION

This invention relates to novel indole compounds useful for Inflammatory Diseases.

BACKGROUND OF THE INVENTION

The structure and physical properties of human non-pancreatic secretory phospholipase A₂ (hereinafter called, "sPLA₂") has been thoroughly described in two articles, namely, "Cloning and Recombinant Expression of Phospholipase A₂ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase A₂" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

It is believed that sPLA₂ is a rate limiting enzyme in the arachidonic acid cascade which hydrolyzes membrane phospholipids. Thus, it is important to develop compounds which inhibit sPLA₂ mediated release of fatty acids (e.g., arachidonic acid). Such compounds would be of value in general treatment of conditions induced and/or maintained by overproduction of sPLA₂; such as sepsis or rheumatoid arthritis.

It is desirable to develop new compounds and treatments for sPLA₂ induced diseases.

SUMMARY OF THE INVENTION

This invention provides novel indole compounds having potent and selective effectiveness as inhibitors of mammalian sPLA₂.

This invention is also the use of novel indole compounds useful in the treatment and prevention of Inflammatory Diseases.

This invention is also the use of novel of indole compounds to inhibit mammalian sPLA₂ mediated release of fatty acids.

This invention is also a pharmaceutical composition containing any of the indole compounds of the invention.

I. Definitions:

The term, "Inflammatory Diseases" refers to diseases such as inflammatory bowel disease, sepsis, septic shock, adult respiratory distress syndrome, pancreatitis, trauma-induced shock, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit sPLA₂ mediated release of fatty acid and to thereby inhibit or prevent the arachidonic acid cascade and its deleterious products.

The term, "indole nucleus" refers to a nucleus (having numbered positions) with the structural formula (X):

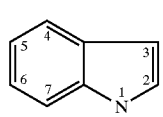

The indole compounds of the invention employ ertain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, sec-butyl, n-pentyl, and n-hexyl.

The term, "alkenyl" employed alone or in combination with other terms means a straight chain or branched monovalent hydrocarbon group having the stated number range of carbon atoms, and typified by groups such as vinyl, propenyl, crotonyl, isopentenyl, and various butenyl isomers.

The term, "hydrocarbyl", means an organic group containing only carbon and hydrogen.

The term, "halo" means fluoro, chloro, bromo, or iodo. The term, heterocyclic radical, refers to radicals derived from monocyclic or polycyclic, saturated or unsaturated, substituted or unsubstituted heterocyclic. nuclei having 5 to 14 ring atoms and containing from 1 to 3 hetero atoms selected from the group consisting of nitrogen, oxygen or sulfur. Typical heterocyclic radicals are pyrrolyl, pyrrolodinyl, piperidinyl, furanyl, thiophenyl, pyrazolyl, imidazolyl, phenylimidazolyl, riazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridylyl. phenylpyridinyl, benzylpyridinyl, pyrimidinyl, phenylpyrimidinyl, pyrazinyl, 1,3,5-triazinyl, quinolinyl, phthalazinyl, quinazolinyl,morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiopheneyl, pentamethylenesulfadyl, 1,3-dithianyl, 1,4-dithianyl, 1,4-thioxanyl, azetidinyl, hexamethyleneiminium, heptamethyleneiminium, piperazinyl and quinoxalinyl.

The term, "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, spiro[5.5]undecanyl, naphthyl, norbornanyl, bicycloheptadienyl, tolulyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (a):

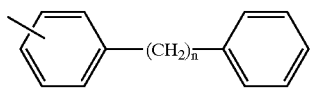

(a)

where n is a number from n 1 to 8.

The term, "non-interfering substituent", refers to radicals suitable for substitution at positions 4,5,6 and/or 7 of the indole nucleus and on other nucleus substituents (as hereinafter described for Formula I), and radicals suitable for substitution on the heterocyclic radical and carbocyclic radical as defined above. Illustrative non-interfering radicals are $C_1$–$C_8$ alkyl, $C_2$–$C_8$ alkenyl, $C_2$–$C_8$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_8$ alkoxy, $C_2$–$C_8$ alkenyloxy, $C_2$–$C_8$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_8$ alkylsulfinyl, $C_1$–$C_8$ alkylsulfonyl, $C_2$–$C_8$ haloalkoxy, $C_1$–$C_8$ haloalkylsulfonyl, $C_2$–$C_8$ haloalkyl, $C_1$–$C_8$ hydroxyalkyl, —C(O)O($C_1$–$C_8$ alkyl), —$(CH_2)_n$—O—($C_1$–$C_8$ alkyl), benzyloxy, phenoxy, phenylthio, —(CONHSO$_2$R), —CHO, amino, amidino, bromo, carbamyl, carboxyl, carbalkoxy, —$(CH_2)_n$—$CO_2$H, chloro, cyano, cyanoguanidinyl, fluoro, guanidino, hydrazide, hydrazino, hydrazido, hydroxy, hydroxyamino, iodo, nitro, phosphono, —$SO_3$H, thioacetal, thiocarbonyl, and carbonyl; where n is from 1 to 8 and R is $C_1$–$C_8$ alkyl.

The term, "organic substituent" refers to a monovalent radical consisting of carbon and hydrogen with or without oxygen, nitrogen, sulfur, halogen, or other elements. Illustrative organic substituents are $C_1$–$C_8$ alkyl, aryl, $C_7$–$C_{14}$ aralkyl, $C_7$–$C_{14}$ alkaryl, $C_3$–$C_8$ cycloalkyl, $C_1$–$C_8$ alkoxyalkyl and these groups substitued with halogen, —$CF_3$, —OH, $C_1$–$C_8$ alkyl, amino, carbonyl, and —CN.

The term, "acylamino acid group" is represented by the formula:

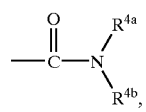

wherein $R^{4a}$ is selected from the group consisting of H, ($C_1$–$C_6$)alkyl, ($C_1$–$C_6$)alkoxy, heteroaryl and aryl, —$CF_3$; and wherein $NR^{4b}$ is an amino acid residue of either a natural or unnatural amino acid with the nitrogen atom being part of the amino group of the amino acid. A typical amino acid is selected from the group comprising isoleucine, valine, phenylalanine, aspartic acid, leucine, glycine, asparagine, cystein, glutamine, glutamic acid, histidine, lysine, methionine, serine, threonine, tryptophan, tyrosine and derivatives thereof. Also contemplated within the definition of amino acid is l-proline, d-proline and derivatives thereof. Also contemplated within the definition of amino acids are peptides, polypeptides and derivatives thereof.

The term "substituted group" is an organic group substituted with one or more non-interfering substituents.

The terms, "amino acid residue" refer to the portion of the amino acid group coupled at the nitrogen atom of the amino terminus. It is the amino acid less a hydrogen atom from the amino terminus. It is further illustrated as used herein for the amino acid alanine attached at the nitrogen atom as shown below:

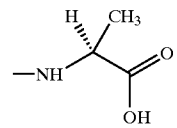

The words, "acylamino acid linker" refer to a divalent linking group symbolized as, —($L_c$)—, which has the function of joining the 4-position of the indole nucleus to an acylamino acid group in the general relationship:

The words, "acylamino acid linker length", refer to the number of atoms (excluding hydrogen) in the shortest chain of the linking group —($L_c$)— that connects the 4-position of the indole nucleus with the acylamino acid group. The presence of a carbocyclic ring in —($L_c$)— counts as the number of atoms approximately equivalent to the calculated diameter of the carbocyclic ring. Thus, a benzene or cyclohexane ring in the acid linker counts as 2 atoms in calculating the length of —($L_c$)—. Illustrative acylamino acid linker groups are;

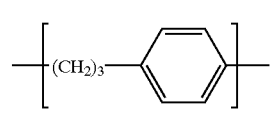

(a)

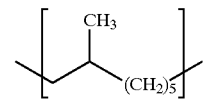

(b)

(c)

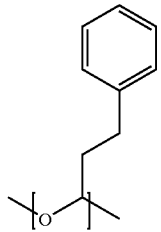

wherein, groups (a), (b) and (c) have acid linker lengths of 5, 7, and 2, respectively.

The term, "(acidic group)" means an organic group which when attached to an indole nucleus at position 5, through suitable linking atoms (hereinafter defined as the "acid linker"), acts as a proton donor capable of hydrogen bonding. Illustrative of an (acidic group) are the following:

-5-tetrazolyl,

—SO$_3$H,

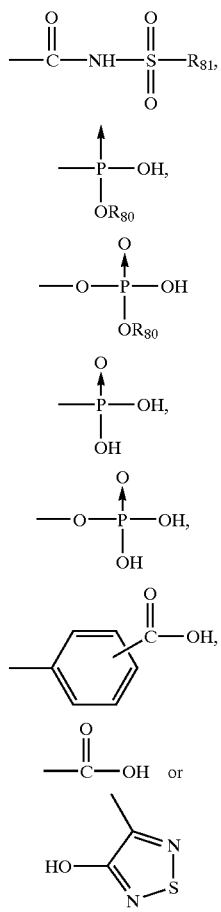

where n is 1 to 8, R$_{80}$ is a metal or C$_1$–C$_8$ and R$_{81}$ is an organic substituent or —CF$_3$.

The words, "acid linker" refer to a divalent linking group symbolized as, —(L$_a$)—, which has the function of joining the 5 position of the indole nucleus to an acidic group in the general relationship:

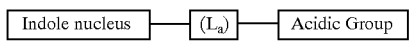

The words, "acid linker length", refer to the number of atoms (excluding hydrogen) in the shortest chain of the linking group —(L$_a$)— that connects the 5 position of the indole nucleus with the acidic group. The presence of a carbocyclic ring in —(L$_a$)— counts as the number of atoms approximately equivalent to the calculated diameter of the carbocyclic ring. Thus, a benzene or cyclohexane ring in the acid linker counts as 2 atoms in calculating the length of —(L$_a$)—. Illustrative acid linker groups are;

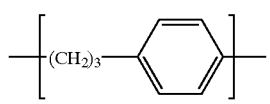
(a)

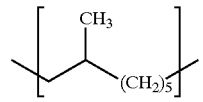
(b)

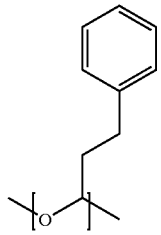
(c)

wherein, groups (a), (b), and (c) have acid linker lengths of 5, 7, and 2, respectively.

The term, "amine", includes primary, secondary and tertiary amines.

The terms, "mammal" and "mammalian" include human and domesticated quadrupeds.

The term, "alkylene chain of 1 or 2 carbon atoms" refers to the divalent radicals, —CH$_2$—CH$_2$— and —CH$_2$—.

The term, "group containing 1 to 4 non-hydrogen atoms" refers to relatively small groups which form substituents at the 2 position of the indole nucleus, said groups may contain non-hydrogen atoms alone, or non-hydrogen atoms plus hydrogen atoms as required to satisfy the unsubstituted valence of the non-hydrogen atoms, for example; (i) groups absent hydrogen which contain no more than 4 non-hydrogen atoms such as —CF$_3$, —Cl, —Br, —NO$_2$, —CN, —SO$_3$; and (ii) groups having hydrogen atoms which contain less than 4 non-hydrogen atoms such as —CH$_3$, —C$_2$H$_5$, and —CH=CH$_2$.

The term "oxime amide" means the radical, —C=NOR—C(O)NH$_2$

The term "thio-oxime amide" means the radical —C=NOR—C(S)—NH$_2$.

The term "spiro[5.5]undecanyl" refers to the group represented by the formula;

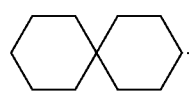

II. The amino acid 1H-indole Compounds of the Invention:

The present invention provides novel classes of indole compounds useful as sPLA$_2$ inhibitors for the treatment of inflammation. Classes of indole compounds of this invention include indole glyoxylamide amino acid derivatives, indole-3-oxime amide amino acid derivatives and indole acetamide amino acid derivatives. The compounds of the invention have the general formula (I) or a pharmaceutically acceptable salt, solvate or prodrug thereof;

(I)

[Structure: indole with substituents R4, R5, R3, R6, R7, R2, R1, N]

wherein;
$R_1$ is selected from groups (a), (b), and (c) wherein;
- (a) is $C_7$–$C_{20}$ alkyl, $C_7$–$C_{20}$ haloalkyl, $C_7$–$C_{20}$ alkenyl, $C_7$–$C_{20}$ alkynyl, carbocyclic radical, or heterocyclic radical, or
- (b) is a member of (a) substituted with one or more independently selected non-interfering substituents; or
- (c) is the group —($L_1$)—$R_{11}$; where, —($L_1$)— is a divalent linking group of 1 to 8 atoms and where $R_{11}$ is a group selected from (a) or (b);

$R_2$ is hydrogen, or a group containing 1 to 4 non-hydrogen atoms plus any required hydrogen atoms;

$R_3$ is —($L_3$)— Z, where —($L_3$)— is a divalent linker group selected from a bond or a divalent group selected from:

—CH$_2$—, —O—, —S—, —NH—, or —C(=O)— and Z is selected from an oxime amide or oxime thioamide group represented by the formulae,

[Three structures with NOR$_a$/X/NH$_2$, X/O/NH$_2$, R$_a$/R$_a$/X/NH$_2$]

wherein X is oxygen or sulfur, $R_a$ is independently selected from hydrogen, $C_1$–$C_8$ alkyl, aryl, $C_1$–$C_8$ alkaryl, $C_1$–$C_8$ alkoxy, aralkyl and —CN;

$R_4$ is the group, —($L_c$)—(acylamino acid group); wherein —($L_c$)—, is an acylamino acid linker having an acylamino acid linker length of 1 to 8;

$R_5$ is selected from hydrogen, a non-interfering substituent, or the group, —($L_a$)—(acidic group); wherein —($L_a$)—, is an acid linker having an acid linker length of 1 to 8.

$R_6$ and $R_7$ are selected from hydrogen, non-interfering substituent, carbocyclic radical, carbocyclic radical substituted with non-interfering substituent(s), heterocyclic radicals, and heterocyclic radical substituted with non-interfering substituent(s).

PREFERRED SUBGROUPS OF COMPOUNDS OF FORMULA (I)

Preferred $R_1$ Substituents

A preferred subclass of compounds of formula (I) are those where for $R_1$ the divalent linking group —($L_1$)— is a group represented by any one of the following formulae (Ia), (Ib), (Ic), (Id), (Ie), or (If):

—CH$_2$—, (Ia)

—O—, (Ib)

—S—, (Ic)

—NH— or (Id)

—C(=O)— or (Ie)

$\left(-(Q_1)-C(R_{10})(R_{10})-\right)$ (If)

where $Q_1$ is a bond or any of the divalent groups (Ia), (Ib), (Ic), (Id), (Ie), and (If) and each $R_{10}$ is independently hydrogen, $C_{1-8}$ alkyl, $C_{1-8}$ haloalkyl or $C_{1-8}$ alkoxy.

Particularly preferred as the linking group —($L_1$)— of $R_1$ is an alkylene chain of 1 or 2 carbon atoms, namely, —(CH$_2$)— or —(CH$_2$—CH$_2$)—.

The preferred group for $R_{11}$ is a substituted or unsubstituted group selected from the group consisting of $C_5$–$C_{14}$ cycloalkyl, $C_5$–$C_{14}$ cycloalkenyl, phenyl, naphthyl, norbornanyl, bicycloheptadienyl, tolulyl, xylenyl, indenyl, stilbenyl, terphenylyl, diphenylethylenyl, phenylcyclohexenyl, acenaphthylenyl, and anthracenyl, biphenyl, bibenzylyl and related bibenzylyl homologues represented by the formula (a);

[Structure: phenyl—(CH$_2$)$_n$—phenyl] (a)

where n is a number from 1 to 8.

Particularly preferred are compounds wherein for $R_1$ the combined group —($L_1$)—$R_{11}$ is selected from the group consisting of —(CH$_2$)$_{1-2}$—phenyl(R$_{12}$)$_t$ or —(CH$_2$)$_{1-2}$—phenyl(R$_{12}$)$_u$—(CH$_2$)$_{0-2}$—phenyl(R$_{12}$)$_t$ where $R_{12}$ is a radical independently selected from halo, $C_{1-8}$ alkyl, $C_{1-8}$ alkoxy, —S—($C_1$–$C_8$ alkyl), —O—($C_1$–$C_8$ alkyl) and $C_1$–$C_8$ haloalkyl where t is a number from 0 to 5 and u is a number from 0 to 4 is the group —($L_1$)—$R_{11}$; where, —($L_1$)— is a divalent linking group of 1 to 8 atoms and where $R_{11}$ is a group selected from (a) or (b).

Preferred for $R_{11}$ is —(CH$_2$)m-$R^{12}$ wherein m is an integer from 1 to 6, and $R^{12}$ is (d) a group represented by the formula:

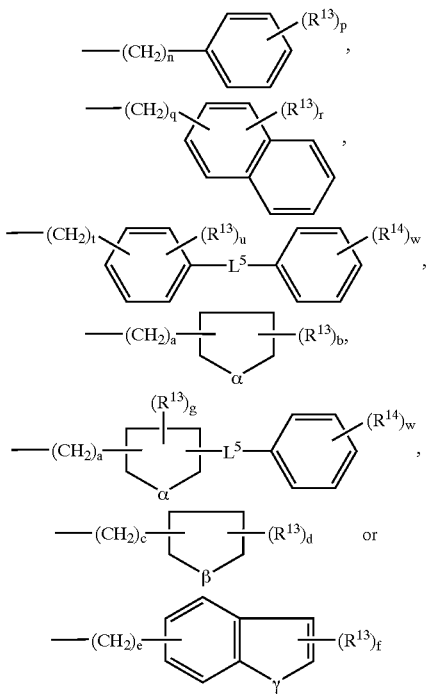

wherein a, c, e, n, q, and t are independently an integer from 0 to 2, $R^{13}$ and $R^{14}$ are independently selected from a halogen, $C_1$ to $C_8$ alkyl, $C_1$ to $C_8$ alkyloxy, $C_1$ to $C_8$ alkylthio, aryl, heteroaryl, and $C_1$ to $C_8$ haloalkyl, α is an oxygen atom or a sulfur atom, $L^5$ is a bond, —$(CH_2)v$-, —C=C—, —CC—, —O—, or —S—, v is an integer from 0 to 2, β is —$CH_2$— or —$(CH_2)_2$—, γ is an oxygen atom or a sulfur atom, b is an integer from 0 to 3, d is an integer from 0 to 4, f, p, and w are independently an integer from 0 to 5, r is an integer from 0 to 7, and u is an integer from 0 to 4, or is (e) a member of (d) substituted with at least one substituent selected from the group consisting of $C_1$ to $C_6$ alkyl, $C_1$ to $C_8$ alkyloxy, $C_1$ to $C_8$ haloalkyloxy, $C_1$ to $C_8$ haloalkyl, aryl, and a halogen.

Preferred $R_2$ Substituentas $R_2$ is preferably selected from the group consisting of hydrogen, $C_1$–$C_4$ alkyl, $C_2$–$C_4$ alkenyl, —O—($C_1$–$C_3$ alkyl), —S—($C_1$–$C_3$ alkyl), —$C_3$–$C_4$ cycloalkyl —$CF_3$, halo, —$NO_2$, —CN, —$SO_3$. Particularly preferred $R_2$ groups are selected from hydrogen, methyl, ethyl, propyl, isopropyl, cyclopropyl, —F, —$CF_3$, —Cl, —Br, or —O—$CH_3$.

Preferred $R_3$ Substituents

A preferred subclass of compounds of formula (I) are those wherein X is oxygen.

Another preferred subclass of compounds of formula (I) are those wherein Z is an oxime amide group.

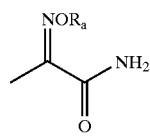

Also preferred are compounds of formula (I) wherein $R_3$ is an oxime amide group and $R_a$ is hydrogen, methyl or ethyl.

For the group $R_3$ it is preferred that the linking group —($L_3$)— be a bond.

Preferred $R_4$ Substituents

Another preferred subclass of compounds of formula (I) are those wherein $R_4$ is a substituent having an acylamino acid linker with an acylamino acid linker length of 2 or 3 and the acylamino acid linker group, —($L_c$)—, for $R_4$ is selected from a group represented by the formula;

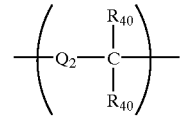

where $Q_2$ is selected from the group —($CH_2$)—, —O—, —NH—, —C(O)—, and —S—, and each $R_{40}$ is independently selected from hydrogen, $C_1$–$C_8$ alkyl, aryl, $C_1$–$C_8$ alkaryl, $C_1$–$C_8$ alkoxy, aralkyl, and halo. Most preferred are compounds where the acylamino acid linker, —($L_c$)—, for $R_4$ is selected from the specific groups;

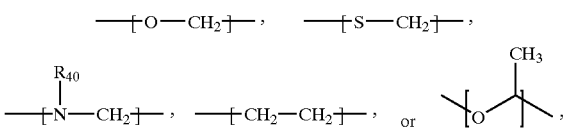

where $R_{40}$ is hydrogen or $C_1$–$C_8$ alkyl. Preferred as the (acylamino acid group) in the group $R_4$ is the group:

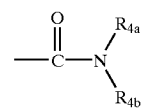

wherein $R^{4a}$ is selected from the group consisting of H, ($C_1$–$C_6$)alkyl, ($C_1$–$C_6$)alkoxy, heteroaryl and aryl; and wherein $NR^{4b}$ is an amino acid residue of either a natural or unnatural amino acid with the nitrogen atom being part of the amino group of the amino acid. A preferred $R^{4a}$ group is the group hydrogen (H). A preferred source of amino acid residue is the amino acid group selected from the group comprising isoleucine, valine, phenylalanine, aspartic acid, leucine, glycine and isomers and derivatives thereof. A salt or a prodrug derivative of the (acylamino acid group) is also a suitable substituent.

Particularly preferred are $R_4$b groups that combine with the nitrogen atom to represent amino acid residues from the amino acid groups selected from: glycine, glycine methyl ester, L-alaninie, L-alanine methylester,L-leucine, L-leucine methyl ester, L-aspartic acid, L-aspartic acid dimethyl ester, L-phenyl alanine, L-phenylalanine methyl ester, malonic acid, malonic acid dimethylester, L-valine, L-valine methyl ester, L-isoleucine, L-isoleucine methyl ester, or salt, and derivatives thereof.

Preferred R₅ Substituents

Preferred acid linker, —(L$_a$)—, for R$_5$ is selected from the group consisting of;

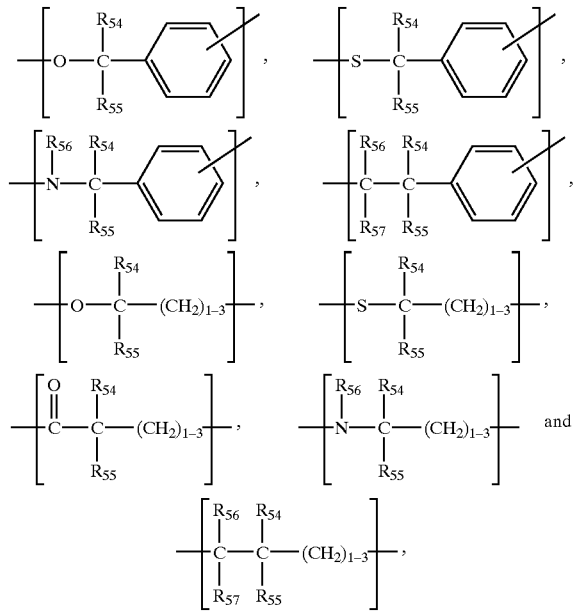

wherein R$_{54}$, R$_{55}$, R$_{56}$ and R$_{57}$ are each independently hydrogen, C$_1$–C$_8$ alkyl, C$_1$–C$_8$ haloalkyl, aryl, C$_1$–C$_8$ alkoxy, or halo. Preferred (acidic group) for R$_5$ is selected from the group consisting of —CO$_2$H, —SO$_3$H and —P(O)(OH)$_2$.

Preferred R₆ and R₇ Substituents

Another preferred subclass of compounds of formula (I) are those wherein for R$_6$ and R$_7$ the non-interfering substituent is independently methyl, ethyl, propyl, isopropyl, thiomethyl, —O-methyl, C$_4$–C$_6$ alkyl, C$_2$–C$_6$ alkenyl, C$_2$–C$_6$ alkynyl, C$_7$–C$_{12}$ aralkyl, C$_7$–C$_{12}$ alkaryl, C$_3$–C$_8$ cycloalkyl, C$_3$–C$_8$ cycloalkenyl, phenyl, tolulyl, xylenyl, biphenyl, C$_1$–C$_6$ alkoxy, C$_2$–C$_6$ alkenyloxy, C$_2$–C$_6$ alkynyloxy, C$_2$–C$_{12}$ alkoxyalkyl, C$_2$–C$_{12}$ alkoxyalkyloxy, C$_2$–C$_{12}$ alkylcarbonyl, C$_2$–C$_{12}$ alkylcarbonylamino, C$_2$–C$_{12}$ alkoxyamino, C$_2$–C$_{12}$ alkoxyaminocarbonyl, C$_1$–C$_{12}$ alkylamino, C$_1$–C$_6$ alkylthio, C$_2$–C$_{12}$ alkylthiocarbonyl, C$_1$–C$_6$ alkylsulfinyl, C$_1$–C$_6$ alkylsulfonyl, C$_2$–C$_6$ haloalkoxy, C$_1$–C$_6$ haloalkylsulfonyl, C$_2$–C$_6$ haloalkyl, C$_1$–C$_6$ hydroxyalkyl, —C(O)O(C$_1$–C$_6$ alkyl), —(CH$_2$)$_n$—O—(C$_1$–C$_6$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and carbonyl; where n is from 1 to 8.

Most preferred as non-interfering substituents are methyl, ethyl, propyl, and isopropyl.

Preferred compounds of the invention are those having the general formula (II), or a pharmaceutically acceptable salt, solvate or prodrug derivative thereof;

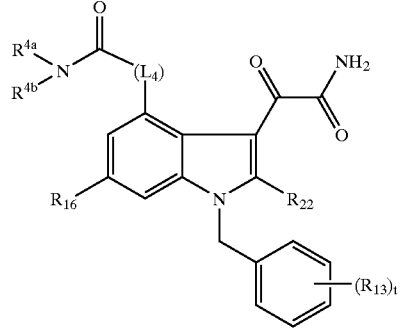

wherein;

R$_{22}$ is selected from hydrogen, methyl, ethyl, propyl, isopropyl, cyclopropyl, —F, —CF$_3$, —Cl, —Br, or —O—CH$_3$;

wherein R$^{4a}$ is selected from the group consisting of H, (C$_1$–C$_6$)alkyl, (C$_1$–C$_6$)alkoxy, heteroaryl and aryl; and wherein NR$^{4b}$ is an amino acid residue of either a natural or unnatural amino acid with the nitrogen atom being part of the amino group of the amino acid. A preferred R$^{4a}$ group is the group hydrogen (H); and —(L$_4$)— is a divalent group selected from;

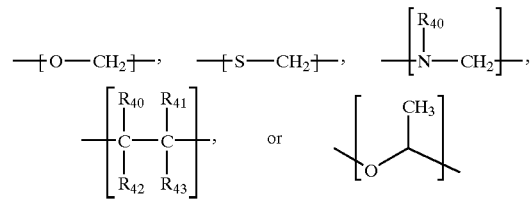

where R$_{40}$, R$_{41}$, R$_{42}$, and R$_{43}$ are each independently selected from hydrogen or C$_1$–C$_8$ alkyl.

R$_{16}$ is selected from hydrogen, C$_1$–C$_8$ alkyl, C$_1$–C$_8$ alkoxy, C$_1$–C$_8$ alkylthio C$_1$–C$_8$ haloalkyl, C$_1$–C$_8$ hydroxyalkyl, and halo.

R$_{13}$ is selected from hydrogen and C$_1$–C$_8$ alkyl, C$_1$–C$_8$ alkoxy, —S—(C$_1$–C$_8$ alkyl), C$_1$–C$_8$ haloalkyl, C$_1$–C$_8$, phenyl, halophenyl, hydroxyalkyl, and halo, and t is an integer from 0 to 5.

Preferred specific compounds (and all pharmaceutically acceptable salts, solvates and prodrug derivatives thereof) which are illustrative of the compounds of the invention are as follow:

N-[2-[[3-(Aminooxoacetyl)-2-ethyl-1-(phenylmethyl)-1H-indol-4-yl]oxy]acetyl]glycine;

N-[2-[[3-(Aminooxoacetyl)-2-ethyl-1-(phenylmethyl)-1H-indol-4-yl]oxy]acetyl]glycine methyl ester;

N-[2-[[3-(Aminooxoacetyl)-2-ethyl-1-(phenylmethyl)-1H-indol-4-yl]oxy]acetyl]glycine;

N-[2-[[3-(Aminooxoacetyl)-2-ethyl-1-(phenylmethyl)-1H-indol-4-yl]oxy]acetyl]-L-alanine;

N-[2-[[3-(Aminooxoacetyl)-2-ethyl-1-(phenylmethyl)-1H-indol-4-yl]oxy]acetyl]-L-alanine methyl ester;

N-[2-[[3-(Aminooxoacetyl)-2-ethyl-1-(phenylmethyl)-1H-indol-4-yl]oxy]acetyl]-L-alanine;

N-[2-[[3-(Aminooxoacetyl)-2-ethyl-1-(phenylmethyl)-1H-indol-4-yl]oxy]acetyl]-L-leucine;

N-[2-[[3-(Aminooxoacetyl)-2-ethyl-1-(phenylmethyl)-1H-indol-4-yl]oxy]acetyl]-L-leucine methyl ester;

N-[2-[[3-(Aminooxoacetyl)-2-ethyl-1-(phenylmethyl)-1H-indol-4-yl]oxy]acetyl]-L-leucine;

N-[2-[[3-(Aminooxoacetyl)-2-ethyl-1-(phenylmethyl)-1H-indol-4-yl]oxy]acetyl]-L-aspartic acid;

N-[2-[[3-(Aminooxoacetyl)-2-ethyl-1-(phenylmethyl)-1H-indol-4-yl]oxy]acetyl]-L-aspartic acid dimethyl ester;

N-[2-[[3-(Aminooxoacetyl)-2-ethyl-1-(phenylmethyl)-1H-indol-4-yl]oxy]acetyl]-L-aspartic acid;

N-[2-[[3-(Aminooxoacetyl)-2-ethyl-1-(phenylmethyl)-1H-indol-4-yl]oxy]acetyl]-L-phenylalanine;

N-[2-[[3-(Aminooxoacetyl)-2-ethyl-1-(phenylmethyl)-1H-indol-4-yl]oxy]acetyl]-L-phenylalanine methyl ester;

N-[2-[[3-(Aminooxoacetyl)-2-ethyl-1-(phenylmethyl)-1H-indol-4-yl]oxy]acetyl]-L-phenylalanine;

[2-[[3-(Aminooxoacetyl)-2-ethyl-1-(phenylmethyl)-1H-indol-4-yl]oxy]acetamido]malonic acid;

[2-[[3-(Aminooxoacetyl)-2-ethyl-1-(phenylmethyl)-1H-indol-4-yl]oxy]acetamido]malonic acid dimethyl ester;

[2-[[3-(Aminooxoacetyl)-2-ethyl-1-(phenylmethyl)-1H-indol-4-yl]oxy]acetamido]malonic acid;

N-[2-[[3-(Aminooxoacetyl)-2-ethyl-1-(phenylmethyl)-1H-indol-4-yl]oxy]acetyl]-L-valine;

N-[2-[[3-(Aminooxoacetyl)-2-ethyl-1-(phenylmethyl)-1H-indol-4-yl]oxy]acetyl]-L-valine methyl ester;

N-[2-[[3-(Aminooxoacetyl)-2-ethyl-1-(phenylmethyl)-1H-indol-4-yl]oxy]acetyl]-L-valine;

N-[2-[[3-(Aminooxoacetyl)-2-ethyl-1-(phenylmethyl)-1H-indol-4-yl]oxy]acetyl]-L-isoleucine;

N-[2-[[3-(Aminooxoacetyl)-2-ethyl-1-(phenylmethyl)-1H-indol-4-yl]oxy]acetyl]-L-isoleucine methyl ester; and N-[2-[[3-(Aminooxoacetyl)-2-ethyl-1-(phenylmethyl)-1H-indol-4-yl]oxy]acetyl]-L-isoleucine.

The salts of the above indole compounds represented by formulae (I) and (II) are an additional aspect of the invention. In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound. This changes the racemic form into a mixture of diastereomers and diastereomers, because they have different melting points, different boiling points, and different solubilities can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl; tert-butyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25,099–6).

Morpholinylethyl ester prodrugs may be prepared by reaction of the sodium salt of a compound of Formula (I) (in a medium such as dimethylformamide) 4-(2-chloroethyl) morpholine hydrochloride (available from Aldrich Chemical Co., Milwaukee, Wis. USA, Item No. C4,220-3).

a) The 1H-indole-3-glyoxylamide amino derivative compounds of the invention are prepared by room temperature base catalyzed condensation of the amino acid protected at the acid terminus by protecting group known in the literature but preferably as the methyl ester with the 1H-indole-3-glyoxylamide acid derivative compound of formula (1) as shown in Scheme I:

Scheme 1

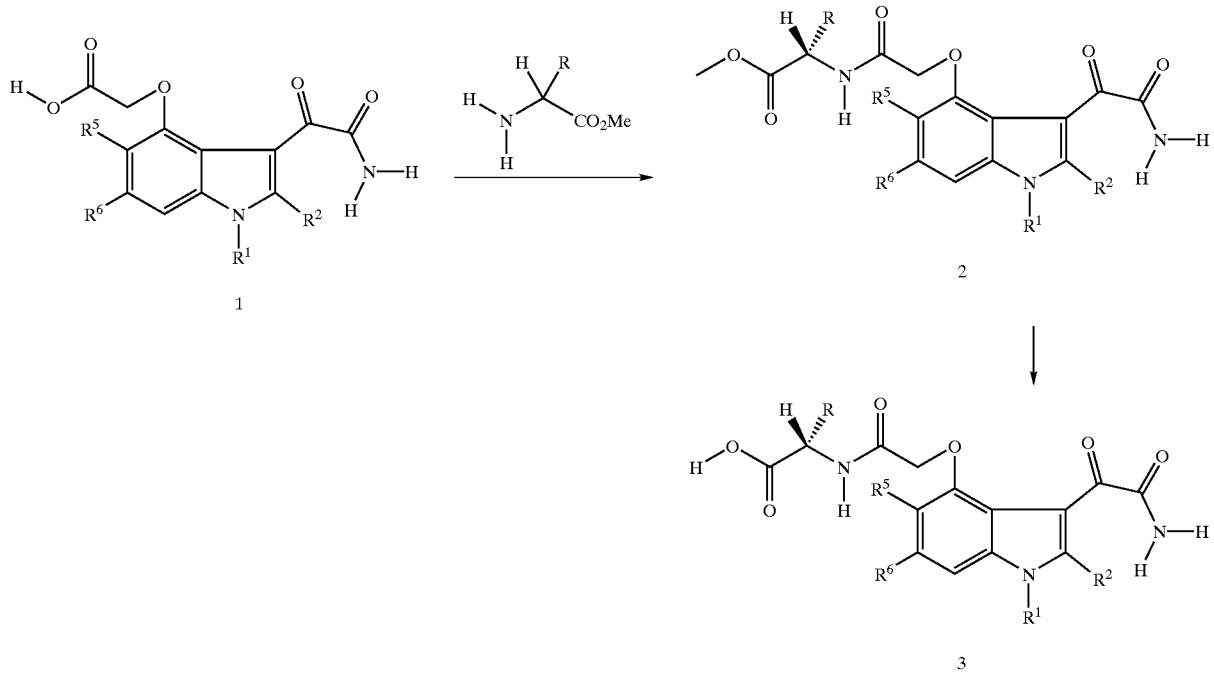

Typically, the condensation or coupling is performed in a solvent such a dimethyl formamide, tetrahydrofuran or aqueous mixtures of the like. In general protic solvents are preferred for the purpose of this invention. The reaction is catalyzed by a base including weak organic or inorganic bases. Organic bases such as collidine are preferred. The reaction is also preferably run in the presence of agents that retard or reduce racemization of the amino acid or its derivative, such as for example, benzotriazolyl-N-oxy-tris (dimethylamino)phosphonium hexafluorophosphate. Upon completion of the reaction, the mixture is concentrated in vacuo. The resulting product mixture is chromatographed to obtain the target compound.

One of skill in the art is aware that the derivatives of the acid such as the acid salt or the methyl ester of the acid, can be reacted with the amino acid or derivatives thereof to obtain the protected compound 2 or a corresponding derivative. Such methods are well known in the arts and can be found in reference texts such as for example J. March *Advanced Organic Chemistry*, Wiley Interscience publishers, New York, N.Y., 1985, and R. C. Larock *Comprehensive Organic Transformations*, VCH Publishers, New York, N.Y., 1989. The protected compounds of formula (2) are also useful sPLA$_2$ inhibitors and are also compounds of this invention.

b) 1H-indole-3-acetamide amino acid derivative sPLA$_2$ inhibitors are similarly prepared by condensation of the protected amino acid with the 1H-indole-3-acetamide sPLA$_2$ inhibitor. The 1H-indole-3-acetamide sPLA$_2$ inhibitors and methods of making them are set out in U.S. Pat. No. 5,684,034, the entire disclosure of which is incorporated herein by reference. Indole-3-acetamide amino acid derivative sPLA$_2$ inhibitors of this invention are represented by compounds of formula (IIb), and pharmaceutically acceptable salts and prodrug derivatives thereof,

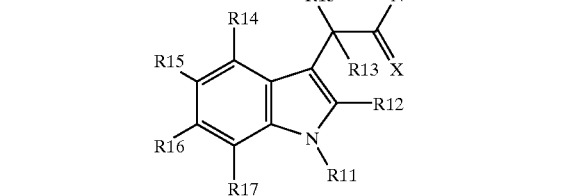

wherein;
X is oxygen or sulfur;
$R_{11}$ is selected from groups (i), (ii) (iii) and (iv) where;
(i) is $C_6$–$C_{20}$ alkyl, $C_6$–$C_{20}$ alkenyl, $C_6$–$C_{20}$ alkynyl, $C_6$–$C_{20}$ haloalkyl, $C_4$–$C_{12}$ cycloalkyl, or
(ii) is aryl or aryl substituted by halo, nitro, —CN, —CHO, —OH, —SH, $C_1$–$C_{10}$ alkyl, $C_1$–$C_{10}$ alkylthio, $C_1$–$C_{10}$ alkoxyl, carboxyl, amino, or hydroxyamino; or
(iii) is —(CH$_2$)$_n$—(R$_{80}$), or —(NH)—(R$_{81}$), where n is 1 to 8, and R$_{80}$ is a group recited in (i), and R$_{81}$ is selected from a group recited in (i) or (ii);
(iv) is

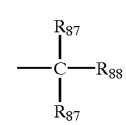

where $R_{87}$ is hydrogen or $C_1$–$C_{10}$ alkyl, and $R_{88}$ is selected from the group; phenyl, naphthyl, indenyl, and biphenyl, unsubstituted or substituted by halo, —CN, —CHO, —OH, —SH, $C_1$–$C_{10}$ alkylthio, $C_1$–$C_{10}$ alkoxyl, phenyl, nitro, $C_1$–$C_{10}$ alkyl, $C_1$–$C_{10}$ haloalkyl, carboxyl, amino, hydroxyamino; or a substituted or unsubstituted 5 to 8 membered heterocyclic ring;

$R_{12}$ is halo, $C_1$–$C_2$ alkylthio, $C_1$–$C_2$ alkyl, $C_1$–$C_2$ alkyaryl or $C_1$–$C_2$ alkoxy;

each $R_{13}$ is independently hydrogen, halo, or methyl;

$R^{14}$ is the group —$L_c$—[acylamino acid], wherein the acylamino acid group is —C(O)—NR$^{14a}$R$^{14b}$ wherein $R_{14a}$ is selected from the group consisting of H, ($C_1$–$C_6$)alkyl, ($C_1$–$C_6$)alkoxy, heteroaryl; and —$L_c$— is as defined supra, and wherein NR$^{14b}$ is an amino acid residue of either a natural or unnatural amino acid with the nitrogen atom being part of the amino group of the amino acid. Most preferred are compounds of formula II wherein the group $R^{14a}$ is a hydrogen atom (H). A preferred source of the amino acid residue NR$^{14b}$ is an amino acid selected from the group comprising isoleucine, valine, phenylalanine, aspartic acid, leucine, glycine and isomers and derivatives thereof;

$R_{15}$ is selected from hydrogen, a non-interfering substituent, or the group, —($L_a$)— (acidic group); wherein —($L_a$)—, is an acid linker having an acid linker length of 1 to 8;

$R_{16}$ and $R_{17}$ are each independently hydrogen, $C_1$–$C_{10}$ alkyl, $C_1$–$C_{10}$ alkenyl, $C_1$–$C_{10}$ alkynyl, $C_3$–$C_8$ cycloalkyl, aryl, aralkyl, or any two adjacent hydrocarbyl groups in the set $R_{15}$, $R_{16}$, and $R_{17}$, combine with the ring carbon atoms to which they are attached to form a 5 or 6 membered substituted or unsubstituted carbocyclic ring; or $C_1$–$C_{10}$ haloalkyl, $C_1$–$C_{10}$ alkoxy, $C_1$–$C_{10}$ haloalkoxy, $C_4$–$C_8$ cycloalkoxy, phenoxy, halo, hydroxy, carboxyl, —SH, —CN, $C_1$–$C_{10}$ alkylthio, arylthio, thioacetal, —C(O)O($C_1$–$C_{10}$ alkyl), hydrazide, hydrazino, hydrazido, —NH$_2$, —NO$_2$, —NR$^{82}$R$_{83}$, and —C(O)NR$_{82}$R$_{83}$, where, R$_{82}$ and R$_{83}$ are independently hydrogen, $C_1$–$C_{10}$ alkyl, $C_1$–$C_{10}$ hydroxyalkyl, or taken together with N, R$_{82}$ and R$_{83}$ form a 5- to 8-membered heterocyclic ring; or a group having the formula;

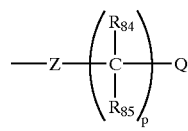

where, $R_{84}$ and $R_{85}$ are each independently selected from hydrogen, $C_1$–$C_{10}$ alkyl, hydroxy, or $R_{84}$ and $R_{85}$ taken together are =O;

p is 1 to 5,

Z is a bond, —O—, —N($C_1$–$C_{10}$ alkyl)—, —NH—, or —S—; and

Q is —CON(R$_{82}$R$_{83}$), -5-tetrazolyl, —SO$_3$H,

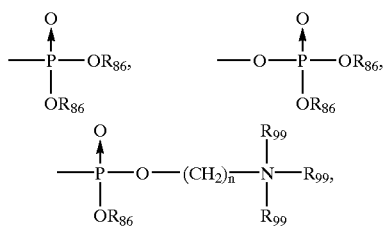

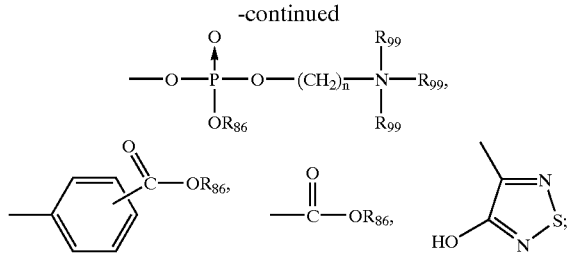

where n is 1 to 8, $R_{86}$ is independently selected from hydrogen, a metal, or $C_1$–$C_{10}$ alkyl, and $R_{99}$ is selected from hydrogen or $C_1$–$C_{10}$ alkyl.

c) Indole-3-Oxime amide compounds of the invention are represented by compounds of formula (III) or a pharmaceutically acceptable salt, solvate or prodrug thereof;

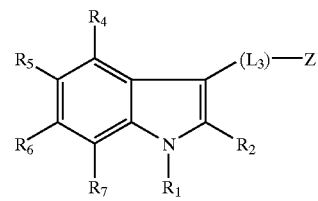

wherein $R_1$ is selected from groups (a), (b), and (c) wherein;
(a) is $C_7$–$C_{20}$ alkyl, $C_7$–$C_{20}$ haloalkyl, $C_7$–$C_{20}$ alkenyl, $C_7$–$C_{20}$ alkynyl, carbocyclic radical, or heterocyclic radical, or
(b) is a member of (a) substituted with one or more independently selected non-interfering substituents; or
(c) is the group —($L_1$)—$R_{11}$; where, —($L_1$)— is a divalent linking group of 1 to 8 atoms and where $R_{11}$ is a group selected from (a) or (b).

Particularly preferred are compounds wherein for $R_1$ the combined group —($L_1$)—$R_{11}$ is selected from the group consisting of

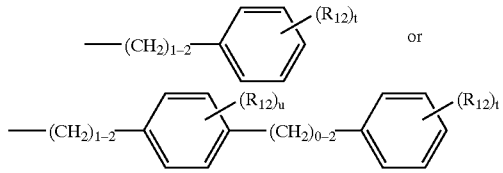

where $R_{12}$ is a radical independently selected from halo, $C_1$–$C_8$ alkyl, $C_1$–$C_8$ alkoxy, —S—($C_1$–$C_8$ alkyl), —O—($C_1$–$C_8$ alkyl) and $C_1$–$C_8$ haloalkyl where t is a number from 0 to 5 and u is a number from 0 to 4.

Also preferred for $R_{11}$ is —(CH$_2$)m-R$^{12}$ wherein m is an integer from 1 to 6, and R$^{12}$ is (d) a group represented by the formula:

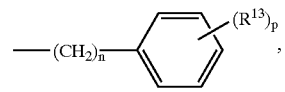

-continued

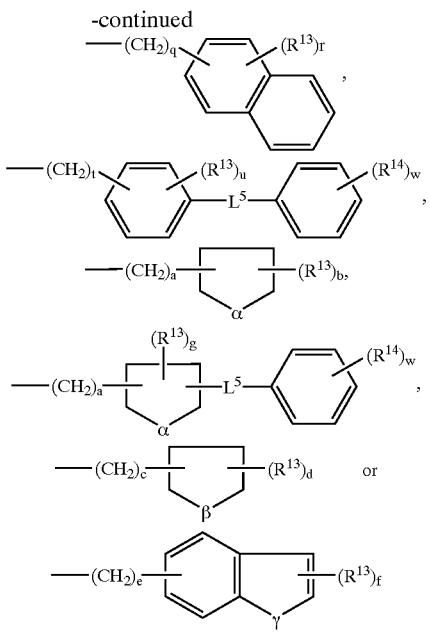

wherein a, c, e, n, q, and t are independently an integer from 0 to 2, $R^{13}$ and $R^{14}$ are independently selected from a halogen, $C_1$ to $C_8$ alkyl, $C_1$ to $C_8$ alkyloxy, $C_1$ to $C_8$ alkylthio, aryl, heteroaryl, and $C_1$ to $C_8$ haloalkyl, α is an oxygen atom or a sulfur atom, $L^5$ is a bond, —(CH$_2$)v-, —C═C—, —CC—, —O—, or —S—, v is an integer from 0 to 2, β is —CH$_2$— or —(CH$_2$)$_2$—, γ is an oxygen atom or a sulfur atom, b is an integer from 0 to 3, d is an integer from 0 to 4, f, p, and w are independently an integer from 0 to 5, r is an integer from 0 to 7, and u is an integer from 0 to 4, or is (e) a member of (d) substituted with at least one substituent selected from the group consisting of $C_1$ to $C_6$ alkyl, $C_1$ to $C_8$ alkyloxy, $C_1$ to $C_8$ haloalkyloxy, $C_1$ to $C_8$ haloalkyl, aryl, and a halogen.

$R_2$ is hydrogen, or a group containing 1 to 4 non-hydrogen atoms plus any required hydrogen atoms;

—(L$_3$)— Z, is the group where —(L$_3$)— is a divalent linker group selected from a bond or a divalent group selected from:

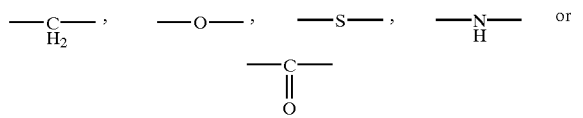

and Z is selected from an oxime amide or oxime thioamide group represented by the formulae,

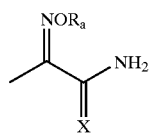

wherein, X is oxygen or sulfur; and $R_a$ is selected from hydrogen, $C_1$–$C_8$ alkyl, aryl, $C_1$–$C_8$ alkaryl, $C_1$–$C_8$ alkoxy, aralkyl and —CN;

$R_4$ is the group, —(L$_c$)—(acylamino acid group); wherein —(L$_c$)—, is an acylamino acid linker having an acylamino acid linker length of 1 to 8;

$R_5$ is selected from hydrogen, a non-interfering substituent, or the group, —(L$_a$)—(acidic group); wherein —(L$_a$)—, is an acid linker having an acid linker length of 1 to 8

$R_6$ and $R_7$ are selected from hydrogen, non-interfering substituent, carbocyclic radical, carbocyclic radical substituted with non-interfering substituent(s), heterocyclic radicals, and heterocyclic radical substituted with non-interfering substituent(s).

PREFERRED SUBGROUPS OF COMPOUNDS OF FORMULA (III)

Preferred $R_1$ Substituents

A preferred subclass of compounds of formula (III) are those where for $R_1$ the divalent linking group —(L$_1$)— is a group represented by any one of the following formulae (Ia), (Ib), (Ic), (Id), (Ie), or (If):

 (Ia)

 (Ib)

 (Ic)

 (Id)

 (Ie)

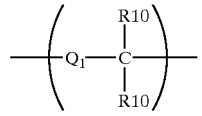 (If)

where $Q_1$ is a bond or any of the divalent groups (Ia), (Ib), (Ic), (Id), (Ie), and (If) and each $R_{10}$ is independently hydrogen, $C_{1-8}$ alkyl, $C_{1-8}$ haloalkyl or $C_{1-8}$ alkoxy.

Particularly preferred as the linking group —(L$_1$)— of $R_1$ is an alkylene chain of 1 or 2 carbon atoms, namely, —(CH$_2$)— or —(CH$_2$—CH$_2$)—.

The preferred group for $R_{11}$ is a substituted or unsubstituted group selected from the group consisting of $C_5$–$C_{14}$ cycloalkyl, $C_5$–$C_{14}$ cycloalkenyl, phenyl, naphthyl, norbornanyl, bicycloheptadienyl, tolulyl, xylenyl, indenyl, stilbenyl, terphenylyl, diphenylethylenyl, phenylcyclohexenyl, acenaphthylenyl, and anthracenyl, biphenyl, bibenzylyl and related bibenzylyl homologues represented by the formula (a);

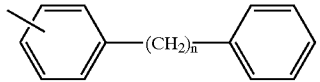 (a)

where n is a number from 1 to 8.

Particularly preferred are compounds wherein for $R_1$ the combined group —(L$_1$)—$R_{11}$ is selected from the group consisting of

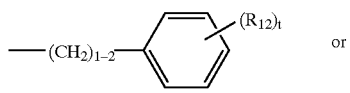 or

-continued

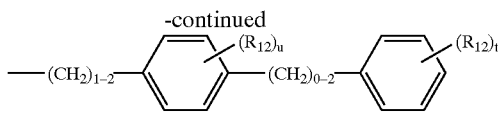

where $R_{12}$ is a radical independently selected from halo, $C_1$-$C_8$ alkyl, $C_1$-$C_8$ alkoxy, —S—($C_1$-$C_8$ alkyl), —O—($C_1$-$C_8$ alkyl) and $C_1$-$C_8$ haloalkyl where t is a number from 0 to 5 and u is a number from 0 to 4.

Also preferred for $R_{11}$ is —(CH$_2$)m-$R^{12}$ wherein m is an integer from 1 to 6, and $R^{12}$ is (d) a group represented by the formula:

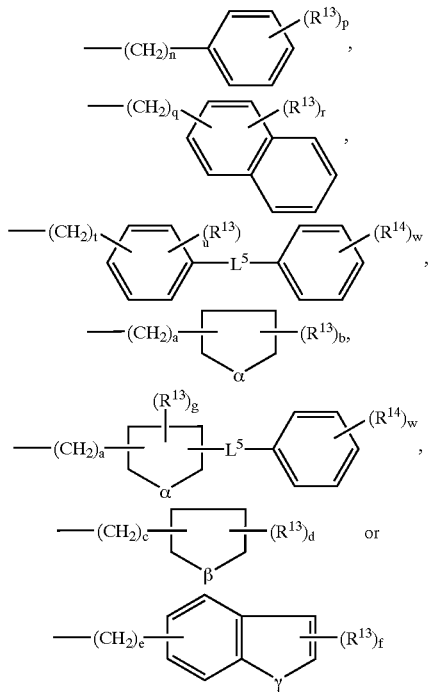

wherein a, c, e, n, q, and t are independently an integer from 0 to 2, $R^{13}$ and $R^{14}$ are independently selected from a halogen, $C_1$ to $C_8$ alkyl, $C_1$ to $C_8$ alkyloxy, $C_1$ to $C_8$ alkylthio, aryl, heteroaryl, and $C_1$ to $C_8$ haloalkyl, α is an oxygen atom or a sulfur atom, $L^5$ is a bond, —(CH$_2$)v-, —C=C—, —CC—, —O—, or —S—, v is an integer from 0 to 2, β is —CH$_2$— or —(CH$_2$)$_2$—, γ is an oxygen atom or a sulfur atom, b is an integer from 0 to 3, d is an integer from 0 to 4, f, p, and w are independently an integer from 0 to 5, r is an integer from 0 to 7, and u is an integer from 0 to 4, or is (e) a member of (d) substituted with at least one substituent selected from the group consisting of $C_1$ to $C_6$ alkyl, $C_1$ to $C_8$ alkyloxy, $C_1$ to $C_8$ haloalkyloxy, $C_1$ to $C_8$ haloalkyl, aryl, and a halogen.

Preferred $R_2$ Substituents $R_2$ is preferably selected from the group consisting of hydrogen, $C_1$-$C_4$ alkyl, $C_2$-$C_4$ alkenyl, —O—($C_1$-$C_3$ alkyl), —S—($C_1$-$C_3$ alkyl), —$C_3$-$C_4$ cycloalkyl —CF$_3$, halo, —NO$_2$, —CN, —SO$_3$. Particularly preferred $R_2$ groups are selected from hydrogen, methyl, ethyl, propyl, isopropyl, cyclopropyl, —F, —CF$_3$, —Cl, —Br, or —0—CH$_3$.

Preferred $R_4$ Substituents

Another preferred subclass of compounds of formula (III) are those wherein $R_4$ is a substituent having an acylamino acid linker with an acylamino acid linker length of 2 or 3 and the acylamino acid linker group, —(L$_c$)—, for $R_4$ is selected from a group represented by the formula;

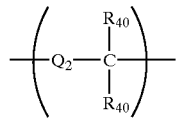

where $Q_2$ is selected from the group —(CH$_2$)—, —O—, —NH—, —C(O)—, and —S—, and each $R_{40}$ is independently selected from hydrogen, $C_1$-$C_8$ alkyl, aryl, $C_1$-$C_8$ alkaryl, $C_1$-$C_8$ alkoxy, aralkyl, and halo. Most preferred are compounds where the acylamino acid linker, —(L$_c$)—, for $R_4$ is selected from the specific groups;

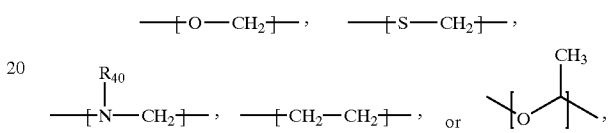

where $R_{40}$ is hydrogen or $C_1$-$C_8$ alkyl. Preferred as the (acylamino acid group) in the group $R_4$ is the group:

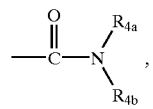

wherein $R^{4a}$ is selected from the group consisting of H, ($C_1$-$C_6$)alkyl, ($C_1$-$C_6$)alkoxy, heteroaryl and aryl; and wherein $NR^{4b}$ is an amino acid residue of either a natural or unnatural amino acid with the nitrogen atom being part of the amino group of the amino acid. A preferred $R^{4a}$ group is the group hydrogen (H). A preferred source of amino acid residue is the amino acid group selected from. the group comprising isoleucine, valine, phenylalanine, aspartic acid, leucine, glycine and isomers and derivatives thereof.

A salt or a prodrug derivative of the (acylamino acid group) is also a suitable substituent.

Particularly preferred are $R^{4b}$ groups that combine with the nitrogen atom to represent amino acid groups selected from: glycine, glycine methyl ester, L-alaninie, L-alanine methylester,L-leucine, L-leucine methyl ester, L-aspartic acid, L-aspartic acid dimethyl ester, L-phenyl alanine, L-phenylalanine methyl ester, malonic acid, malonic acid dimethylester, L-valine, L-valine methyl ester, L-isoleucine, L-isoleucine methyl ester, or salt, and derivatives thereof.

Preferred $R_5$ Substituents

Preferred acid linker, —(L$_a$)—, for $R_5$ is selected from the group consisting of;

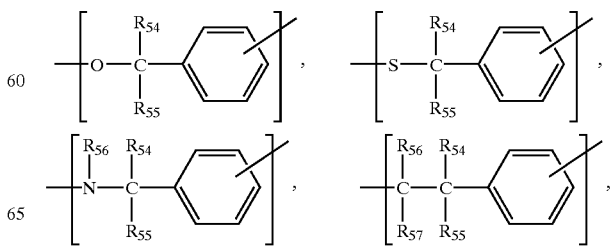

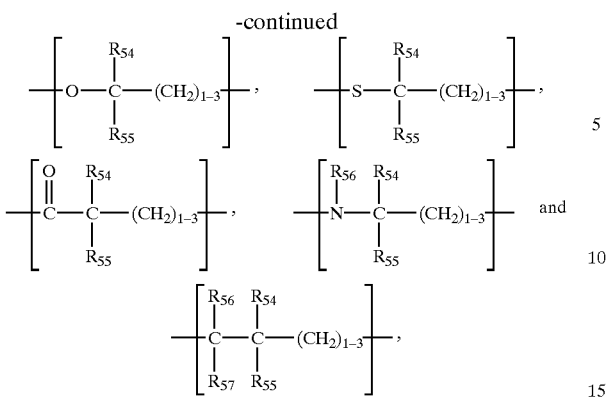

wherein $R_{54}$, $R_{55}$, $R_{56}$ and $R_{57}$ are each independently hydrogen, $C_1$–$C_8$ alkyl, $C_1$–$C_8$ haloalkyl, aryl, $C_1$–$C_8$ alkoxy, or halo. Preferred (acidic group) for $R_5$ is selected from the group consisting of —$CO_2H$, —$SO_3H$ and —$P(O)(OH)_2$

Preferred $R_6$ and $R_7$ Substituents

Another preferred subclass of compounds of formula (III) are those wherein for $R_6$ and $R_7$ the non-interfering substituent is independently methyl, ethyl, propyl, isopropyl, thiomethyl, —O-methyl, $C_4$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —$C(O)O(C_1$–$C_6$ alkyl), —$(CH_2)_n$—O—($C_1$–$C_6$ alkyl), benzyloxy, phenoxy, phenylthio, —($CONHSO_2R$), —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino; hydrazido, hydroxy, hydroxyamino, iodo, nitro, phosphono, —$SO_3H$, thioacetal, thiocarbonyl, and carbonyl; where n is from 1 to 8.

Most preferred as non-interfering substituents are methyl, ethyl, propyl, and isopropyl.

The indole-3-oxime compounds of the invention can be prepared following protocol of scheme 2 below;

Scheme 2

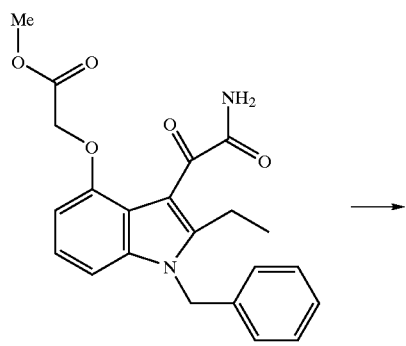

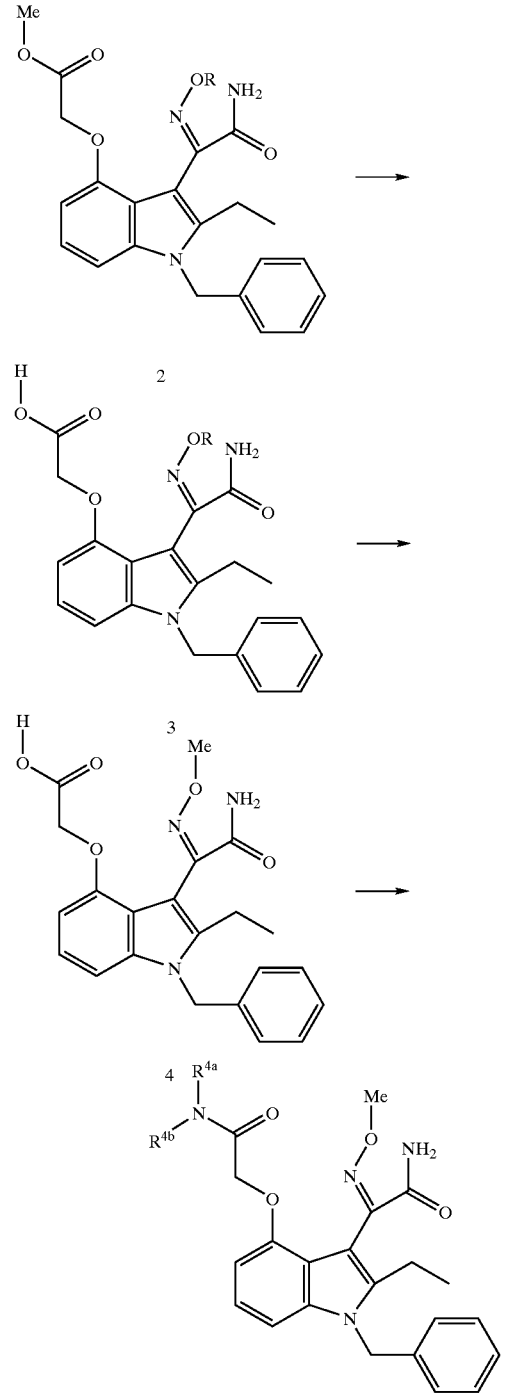

To introduce the oxime functionality, the methyl ester of the glyoxylamide (compound 10 in scheme 1, compound 1 in scheme 2, supra.) is heated with hydroxylamine hydrochloride (when R is H) in a THF/methanol mixture for 8 hours or until the reaction was deemed complete. The reaction product is isolated by chromatography or other known laboratory procedure to afford a white solid. Substituted oximes such as when R is methyl, ethyl, phenyl or other substituent can be prepared by reacting the corresponding substituted hydroxylamine hydrochloride or free base with the glyoxylamide as described supra. The ester functionality at the 4 or 5 position on the indole nucleus, as in for example, compound 2, can be: (a) converted to the acid by hydrolysis using lithium hydroxide or other known ester hydrolysis methods to afford compounds of formula 3, or (b) converted to an amide functionality directly or via the acid functionality to afford compounds of formula 4. General procedures for the conversion of organic acids to amino acid are well known to artisans in the field, and have been documented in general reference texts including, for example, J. March *Advanced Organic Chemistry*, Wiley Interscience publishers, New York, N,Y., 1985, and R. C. Larock *Comprehensive Organic Transformations*, VCH Publishers, New York, N,Y., 1989.

The oxime acid compounds of formula 3 such as the methyloxime compound such as that of formula 4 can be converted to the corresponding amino acid derivative via the methylester by coupling with various amino acids by general coupling procedures known to one skilled in the art. Additional references, or procedures are found in J. March *Advanced Organic Chemistry*, Wiley Interscience publishers, New York, N,Y., 1985; R. C. Larock *Comprehensive Organic Transformations*, VCH Publishers, New York, N,Y., 1989 and J. Jones *Amino Acids and Peptide Synthesis*, Oxford Science Publications, Stephen G. Davis, Editor, Oxford University Press Inc., New York, N.Y., 1992.

III. Method of Making the 1H-Indole-3-Glyoxylamide Starting Material for Preparing the Compounds of the Invention:

The synthesis of the indole compounds of the invention (viz., Compounds of Formulae I and II) can be accomplished by well known methods as recorded in the chemical literature. In particular, the indole starting materials may be prepared by the synthesis schemes taught in U.S. Pat. No. 5,654,326; the disclosure of which is incorporated herein by reference. Another method of making 1H-indole-3-glyoxylamide sPLA$_2$ inhibitors is described in U.S. patent application Ser. No. 09/105381, filed Jun. 26, 1998 and titled, "Process for Preparing 4-substituted 1-H-Indole-3-glyoxyamides" the entire disclosure of which is incorporated herein by reference.

U.S. patent application Ser. No. 09/105381 discloses the following process having steps (a) thru (i)

Preparing a compound of the formula (Iz) or a pharmaceutically acceptable salt or prodrug derivative thereof

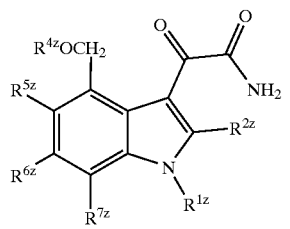

(Iz)

wherein:

R$^{1z}$ is selected from the group consisting of —C$_7$–C$_{20}$ alkyl,

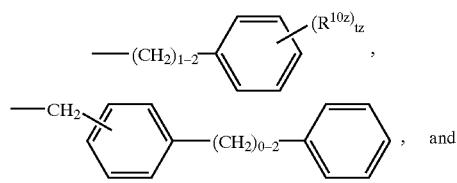, and

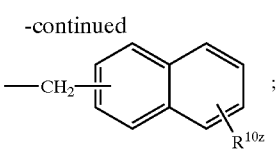

where

R$^{10Z}$ is selected from the group consisting of halo, C$_1$–C$_{10}$ alkyl, C$_1$–C$_{10}$ alkoxy, —S—(C$_1$–C$_{10}$ alkyl) and halo (C$_1$–C$_{10}$ alkyl, and tz is an integer from 0 to 5 both inclusive;

R$^{2z}$ is selected from the group consisting of hydrogen, halo, C$_1$–C$_3$ alkyl, C$_3$–C$_4$ cycloalkyl, C$_3$–C$_4$ cycloalkenyl, —O—(C$_1$–C$_2$ alkyl), —S—(C$_1$–C$_2$ alkyl), aryl, aryloxy and HET;

R$^{4z}$ is the group —CO$_2$H, or salt and prodrug derivative thereof; and

R$^{5z}$, R$^{6z}$ and R$^{7z}$ are each independently selected from the group consisting of hydrogen, (C$_1$–C$_6$)alkyl, (C$_1$–C$_6$) alkoxy, halo(C$_1$–C$_6$)alkoxy, halo(C$_2$–C$_6$)alkyl, bromo, chloro, fluoro, iodo and aryl;

which process comprises the steps of:

a) halogenating a compound of formula Xz

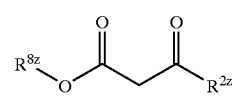

Xz where R$^{8Z}$ is (C$_1$–C$_6$)alkyl, aryl or HET;

with SO$_2$Cl$_2$ to form a compound of formula IX

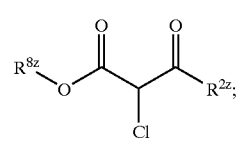

IXz b) hydrolyzing and decarboxylating a compound of formula IXz

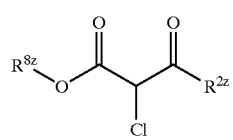

IXz to form a compound of formula VIIIz

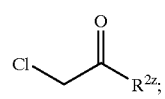

VIIIz c) alkylating a compound of formula VIIz

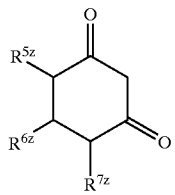

VIIz with a compound of formula VIIIz

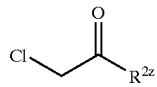

VIIIz to form a compound of formula VIz

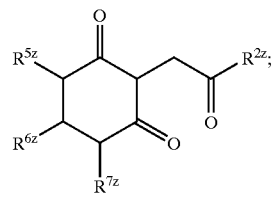

VIz d) aminating and dehydrating a compound of formula VIz

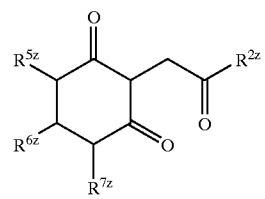

VIz with an amine of the formula $R^{1z}NH_2$ in the presence of a solvent that forms and azeotrope with water to form a compound of formula Vz;

e) oxidizing a compound of formula Vz

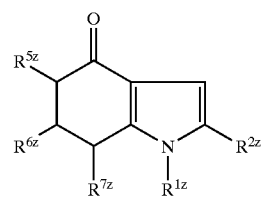

Vz by refluxing in a polar hydrocarbon solvent having a boiling point of at least 150° C. and a dielectric constant of at least 10 in the presence of a catalyst to form a compound of formula IVz

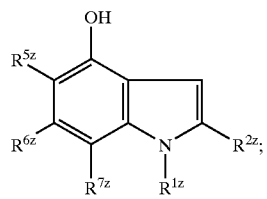

IVz f) alkylating a compound of the formula IVz

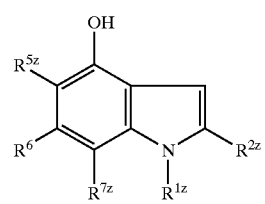

IVz with an alkylating agent of the formula $XCH_2R^{4az}$ where X is a leaving group and $R^{4az}$ is $—CO_2R^{4b}$, where $R^{4bz}$ is an acid protecting group to form a compound of formula IIIz

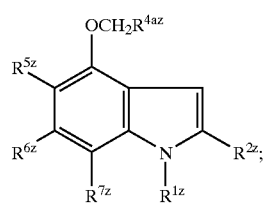

IIIz g) reacting a compound of formula IIIz

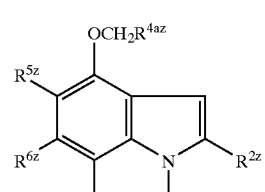

IIIz with oxalyl chloride and ammonia to form a compound of formula IIz

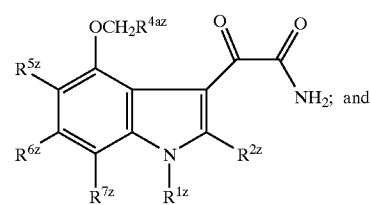

IIz h) optionally hydrolyzing a compound of formula IIz

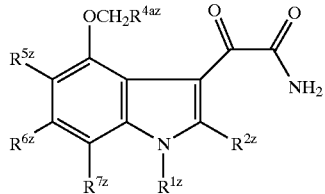

to form a compound of formula Iz.

An alternative protocol useful for the synthesis of the starting material is shown in Scheme 1 below:

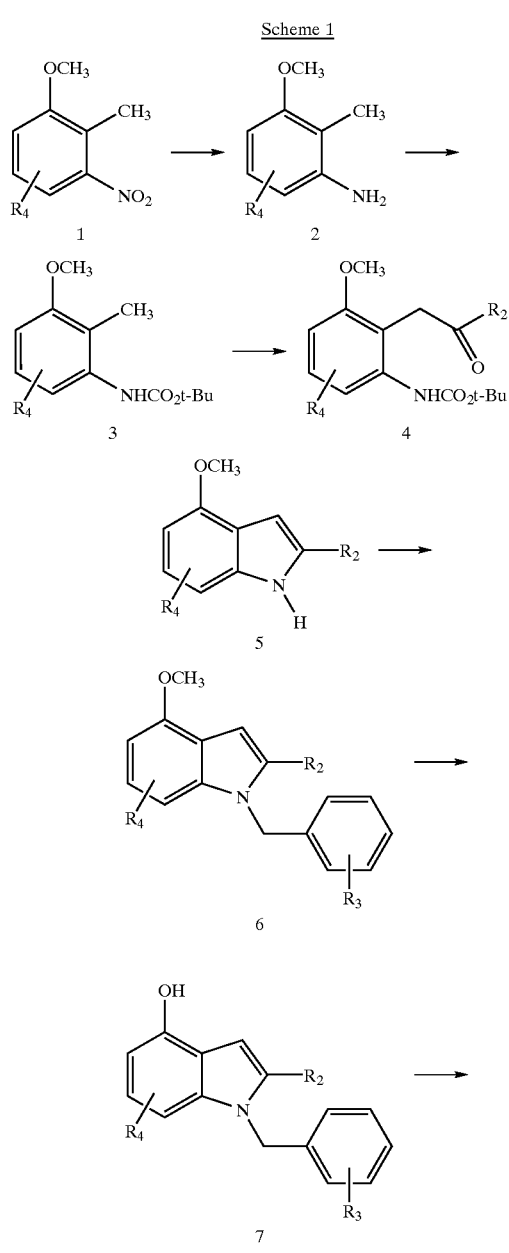

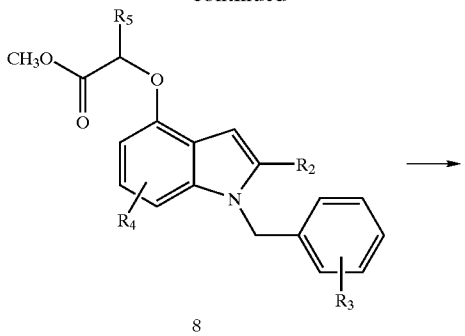

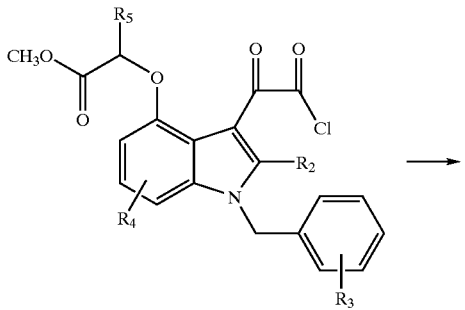

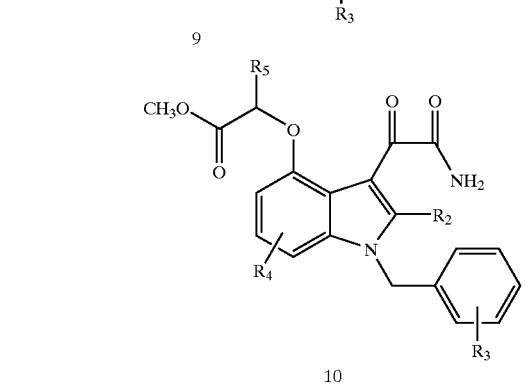

The synthesis of indole-3-oxime amides (compound of formula I and II, supra.) of this invention uses as starting material the glyoxamide ((3(2-amino-1,2-dioxoethyl)-2-methyl-1-(phenylmethyl)-1H-indol-4-yl)oxy)acetic acid methyl ester, compound 10, supra. This starting material is prepared as set out in the preceding section or by the method of Example 9 of U.S. Pat. No. 5,654,326 (the disclosure of which is incorporated herein by reference).

To obtain the glyoxylamide starting material substituted in the 4-position with an (acidic group) linked through an oxygen atom, the reactions outlined in the scheme supra, are used (for conversions 1 through 5, see ref. Robin D. Clark, Joseph M. Muchowski, Lawrence E. Fisher, Lee A. Flippin, David B. Repke, Michel Souchet, *Synthesis*, 1991, 871–878, the disclosures of which are incorporated herein by reference). The starting material ortho-nitrotoluene, 1, is readily reduced to 2-methyl,3-methoxyaniline, 2. Reduction of 1s by the catalytic hydrogenation of the corresponding nitrotoluene using palladium on carbon as catalyst. The reduction can be carried out in ethanol or tetrahydrofuran (THF) or a combination of both, using a low pressure of hydrogen. The aniline 2, obtained, is converted to the N-tert-butyloxycarbonyl derivative 3, in good yield, on heating with di-tert-butyl dicarbonate in THF at reflux temperature. The dilithium salt of the dianion of 3 is generated at −40 to −20° C. in THF using sec-butyllithium and reacted with the appropriately substituted N-methoxy-N-methylalkanamide to form the ketone 4. This product (4) may be purified by crystallization from hexane, or reacted directly with trifluoroacetic acid in methylene chloride to give the 1,3-unsubstituted indole 5. The 1,3-unsubstituted indole 5 is reacted with sodium hydride in dimethylformamide at room temperature (20–25° C.) for 0.5–1.0 hour. The resulting sodium salt of 5 is treated with an equivalent of arylmethyl halide and the mixture stirred at a temperature range of 0–100° C., usually at ambient room temperature, for a period of 4 to 36 hours to give the 1-arylmethylindole, 6. This indole, 6, is O-demethylated by stirring with boron tribromide in methylene chloride for approximately 5 hours (see ref. Tsung-Ying Shem and Charles A Winter, *Adv. Drug Res.*, 1977, 12, 176, the disclosure of which is incorporated herein by reference). The 4-hydroxyindole, 7, is alkylated with an alpha bromoalkanoic acid ester in dimethylformamide (DMF) using sodiumhydride as a base, with reaction condition of 5 to 6. The α-[(indol-4-yl)oxy]alkanoic acid ester, 8, is reacted with oxalyl chloride in methylene chloride to give 9, which is not purified but reacted directly with ammonia to give the glyoxamide 10.

Glyoxamide starting material compounds substituted at the 5 position of the indole nucleus with an (acidic group) may be prepared by methods and starting materials shown in schemes 2 and 3 of U.S. Pat. No. 5,654,326; the disclosure of which is incorporated herein by reference.

IV. Methods of Using the Compounds of the Invention:

The indole compounds described herein are believed to achieve their beneficial therapeutic action principally by direct inhibition of mammalian (including human) sPLA$_2$, and not by acting as antagonists for arachidonic acid, nor other active agents below arachidonic acid in the arachidonic acid cascade, such as 5-lipoxygenases, cyclooxygenases, and etc.

The method of the invention for inhibiting sPLA$_2$ mediated release of fatty acids comprises contacting mammalian sPLA$_2$ with an therapeutically effective amount of indole compounds corresponding to Formulae (I) or (II) as described herein including salt or a prodrug derivative thereof.

Another aspect of this invention is a method for treating Inflammatory Diseases such as inflammatory bowel disease, septic shock, adult respiratory distress syndrome, pancreatitis, trauma, bronchial asthma, allergic rhinitis, rheumatoid arthritis, osteoarthritis, and related diseases which comprises administering to a mammal (including a human) a therapeutically effective dose of the indole compound of the invention (see, formulae I and II).

As previously noted the compounds of this invention are useful for inhibiting sPLA$_2$ mediated release of fatty acids such as arachidonic acid. By the term, "inhibiting" is meant the prevention or therapeutically significant reduction in release of sPLA$_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably compounds of the invention (per Formula I or II) or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the indole compound of the invention together with a pharmaceutically acceptable carrier or diluent therefor. The present pharmaceutical formulations are prepared by known procedures using well known and readily available ingredients.

In making the compositions of the present invention, the Active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of 2 mg/ml in a 4% dextrose/0.5% Na citrate aqueous solution. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active ingredient. In tablets the Active ingredient is mixed with a carrier having the necessary binding properties in suitable proportions and compacted in the shape and size desired. The powders and tablets preferably contain from about 1 to about 99 weight percent of the Active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active ingredient can be dissolved or suspended in a pharmaceutically acceptable carrier, such as sterile water, sterile organic solvent or a mixture of both. The Active ingredient can often be dissolved in a suitable organic solvent, for instance aqueous propylene glycol. Other compositions can be made by dispersing the finely divided Active ingredient in aqueous starch or sodium carboxymethyl cellulose solution or in a suitable oil.

The following pharmaceutical formulations 1 thru 8 are illustrative only and are not intended to limit the scope of the invention in any way. "Active ingredient", refers to a compound according to Formula (I) or (II) or a pharmaceutically acceptable salt, solvate, or prodrug thereof.

FORMULATION 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

FORMULATION 2

A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

FORMULATION 3

An aerosol solution is prepared containing the following components:

|  | Weight |
| --- | --- |
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of Active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of Active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The Active ingredient, cellulose, starch, and magnesium stearate are blended, passed through a No. 45 mesh U.S. sieve, and filled into hard gelatin capsules in 200 mg quantities.

FORMULATION 6

Suppositories, each containing 225 mg of Active ingredient, are made as follows:

| Active ingredient | 225 mg |
| --- | --- |
| Saturated fatty acid glycerides | 2,000 mg |
| Total | 2,225 mg |

The Active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of Active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| | |
|---|---|
| Active ingredient | 100 mg |
| Isotonic saline | 1,000 ml |

The solution of the above ingredients generally is administered intravenously to a subject at a rate of 1 ml per minute.

All of the products of the Examples described below as well as intermediates used in the following procedures showed satisfactory nmr and IR spectra. They also had the correct mass spectral values.

EAXMPLE 1

Preparation of [[3-(2-Amino-1,2-dioxoethyl)-2-ethyl-1-(phenylmethyl)-1H-indol-4-yl]oxy]acetic acid methyl ester, a compound represented by the compound of formula (1) formula:

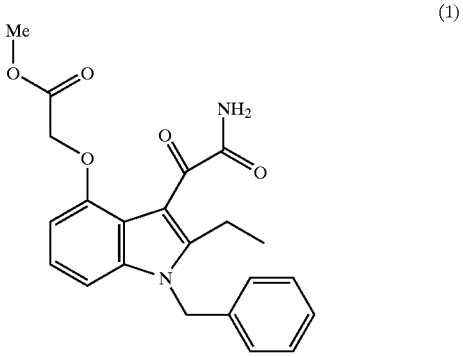

(1)

Part A. Preparation of 2-Ethyl-4-methoxy-1H-indole

A solution of 140 mL (0.18 mol) of 1.3M sec-butyl lithium in cyclohexane was added slowly to N-tert-butoxycarbonyl-3-methoxy-2-methylaniline (21.3 g, 0.09 mol) in 250 mL of THF keeping the temperature below −40° C. with a dry ice-ethanol bath. The bath was removed and the temperature allowed to rise to 0° C. and then the bath replaced. After the temperature had cooled to −60° C., 18.5 g (0.18 mol) of N-methoxy-N-methylpropanamide in an equal volume of THF was added dropwise. The reaction mixture was stirred 5 minutes, the cooling bath removed and stirred an additional 18 hours. It was then poured into a mixture of 300 mL of ether and 400 mL of 0.5N HCl. The organic layer was separated, washed with water, brine, dried over $MgSO_4$, and concentrated at reduced pressure to give 25.5 g of a crude of 1-[2-(tert-butoxycarbonylamino)-6-methoxyphenyl]-2-butanone. This material was dissolved in 250 mL of methylene chloride and 50 mL of trifluoroacetic acid and stirred for a total of 17 hours. The mixture was concentrated at reduced pressure and ethyl acetate and water added to the remaining oil. The ethyl acetate was separated, washed with brine, dried ($MgSO_4$) and concentrated. The residue was chromatographed three times on silica eluting with 20% EtOAc/hexane to give 13.9 g of 2-ethyl-4-methoxy-1H-indole.

Analyses for $C_{11}H_{13}NO$: Calculated: C, 75.40; H, 7.48; N, 7.99; Found: C, 74.41; H, 7.64; N, 7.97.

Part B. Preparation of 2-Ethyl-4-Methoxy-1-(phenylmethyl)-1H-indole

2-Ethyl-4-methoxy-1H-indole (4.2 g, 24 mmol) was dissolved in 30 mL of DMF and 960 mg (24 mmol) of 60% NaH/minerial oil was added. After 1.5 hours, 2.9 mL (24 mmol) of benzyl bromide was added. After 4 hours, the mixture was diluted with water and extracted twice with ethyl acetate. The combined ethyl acetate was washed with brine, dried ($MgSO_4$) and concentrated at reduced pressure. The residue was chromatographed on silica gel and eluted with 20% EtOAc/hexane to give 3.1 g (49% yield) of 2-ethyl-4-methoxy-1-(phenylmethyl)-1H-indole.

Part C. Preparation of 2-Ethyl-4-hydroxy-1-(phenylmethyl)-1H-indole 3.1 g (11.7 mmol) of 2-ethyl-4-methoxy-1-(phenylmethyl)-1H-indole was O-demethylated by treating it with 48.6 mL of 1M $BBr_3$ in methylene chloride with stirring at room temperature for 5 hours, followed by concentration at reduced pressure. The residue was dissolved in ethyl acetate, washed with brine and dried ($MgSO_4$). After concentrating at reduced pressure, the residue was chromatographed on silica gel eluting with 20% EtOAc/hexane to give 1.58 g (54% yield) of 2-ethyl-4-hydroxy-1-(phenylmethyl)-1H-indole, mp, 86–90° C.

Analyses for $C_{17}H_{17}NO$: Calculated: C, 81.24; H, 6.82; N, 5.57; Found: C, 81.08; H, 6.92; N, 5.41.

Part D. Preparation of [[2-Ethyl-1-(phenylmethyl)-1H-indol-4-yl]oxy]acetic Acid Methyl Ester.

2-ethyl-4-hydroxy-1-(phenylmethyl)-1H-indole (1.56 g, 6.2 mmol) was added to a mixture of 248 mg (6.2 mmol.) of 60% NaH/mineral oil in 20 mL DMF and stirred for 0.67 hour.

Then 0.6 mL(6.2 mmol) of methyl bromoacetate was added and stirring was continued for 17 hours. The mixture was diluted with water and extracted with ethyl acetate. The ethyl acetate solution was washed with brine, dried ($MgSO_4$), and concentrated at reduced pressure. The residue was chromatographed on silica gel eluting with 20% EtOAc/hexane, to give 1.37 g (69% yield) of [[2-ethyl-1-(phenylmethyl)-1H-indol-4-yl]oxy]acetic acid inethyl ester, 89–92° C.

Analyses for $C_{20}H_{21}NO_3$: Calculated: C, 74.28; H, 6.55; N, 4.33; Found: C, 74.03; H, 6.49; N, 4.60.

Part E. Preparation of [[3-(2-Amino-1,2-dioxoethyl)-2-ethyl-1-(phenylmethyl)-1H-indol-4-yl]oxy]acetic Acid Methyl Ester.

Oxalyl chloride (0.4 mL, 4.2 nmnol) was added to 1.36 g (4.2 mmol) of [[2-ethyl-1-(phenylmethyl)-1H-indol-4-yl]oxy]acetic acid methyl ester in 10 mL of methylene chloride and the mixture stirred for 1.5 hours. The mixture was concentrated at reduced pressure and residue taken up in 10 mL of methylene chloride. Anhydrous ammonia was bubbled in for 0.25 hours, the mixture stirred for 1.5 hours and evaporated at reduced pressure. The residue was stirred with 20 mL of ethyl acetate and the mixture filtered. The filtrate was concentrated to give 1.37 g of a mixture of [[3-(2-amino-1,2-dioxoethyl)-2-ethyl-1-(phenylmethyl)-1H-indol-4-yl]oxy]acetic acid methyl ester and ammonium chloride. This mixture melted at 172–187° C.

EXAMPLE 2

(indol-3-oxime amide starting material) 2-[[3-[[2-(Aminooxo)-1-(N-hydroxyimino)]ethyl]-2-ethyl-1-(phenylmethyl)-1H-indol-4-yl]oxy]acetic acid.

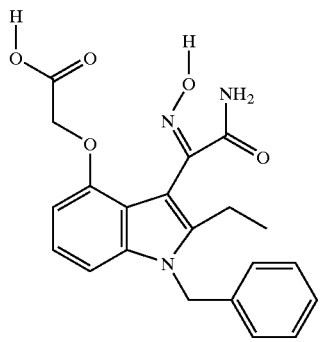

3ai

A. Preparation of 2-[[3-[[2-(Aminooxo)-1-(N-hydroxyimino)]ethyl]-2-ethyl-1-(phenylmethyl)-1H-indol-4-yl]oxy]acetic acid methyl ester.

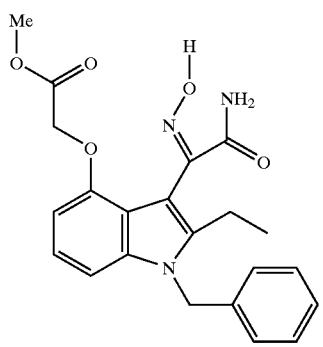

2ai

A stirred mixture of 1 (600 mg, 1.52 mmol) and hydroxylamine hydrochloride (528 mg, 7.60 mmol) in THF (4 mL)/CH$_3$OH (4 mL) was heated at 55° C. for 8 h. After concentration at ambient temperature, the residue was chromatographed on silica (gradient 0–40% EtOAc in CH$_2$Cl$_2$) to give the title compound 2ai (285 mg) as a white solid in 46% yield. IR (CHCl$_3$) 3510, 3415, 1757, 1667 cm$^{-1}$; $^1$H-NMR (CDCl$_3$) δ 1.17 (t, J=7.5 Hz, 3H), 2.84 (q, J=7.5 Hz, 2H), 3.81 (s, 3H), 4.73 (s, 2H), 5.36 (s, 2H), 5.67 (br s, 1H), 6.31 (br s, 1H), 6.41 (d, J=7.8 Hz, 1H), 6.87 (d, J=8.2 Hz, 1H), 6.98–7.07 (m, 3H), 7.23–7.32 (m, 3H); ESIMS m/e 410 (M$^+$+1).

Elemental Analyses for C$_{22}$H$_{23}$N$_3$O$_5$·0.30(H$_2$O): Calculated: C, 63.70; H, 5.73; N, 10.13; Found: C, 63.68; H, 5.62; N, 10.20.

EXAMPLE 3

N-[2-[[3-(Aminooxoacetyl)-2-ethyl-1-(phenylmethyl)-1H-indol-4-yl]oxy]acetyl]glycine

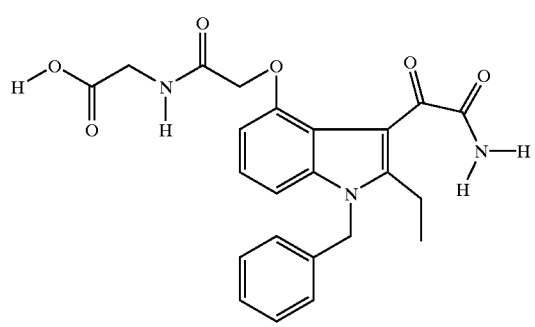

3a

A. Preparation of N-[2-[[3-(Aminooxoacetyl)-2-ethyl-1-(phenylmethyl)-1H-indol-4-yl]oxy]acetyl]glycine Methyl Ester

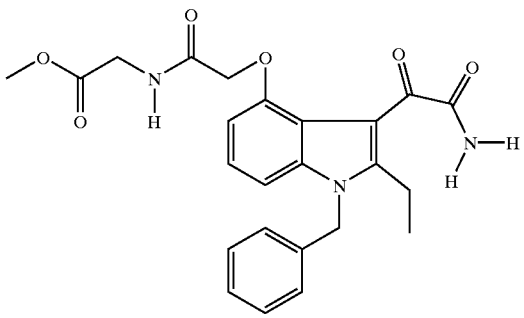

2a

To a solution of 1 (0.100 g, 0.249 mmol) in 2 mL DMF was added collidine (0.069 mL, 0.523 mmol), methyl glycine hydrochloride (0.0313 g, 0.249 mmol), and benzotriazolyl-N-oxy-tris(dimethylamino)phosphonium hexafluorophosphate (0.115 g, 0.261) sequentially at room temperature. After 2.5 hrs. the reaction mixture was concentrated in vacuo to near dryness, then it was taken up in CH$_2$Cl$_2$, chromatographed on a silica gel column (gradient 20–40% THF in CH$_2$Cl$_2$) and dried in an 80° C. vacuum oven to give 0.0768 g of 2a as a yellow solid in 68% yield. $^1$H NMR (DMSO-d$_6$) δ 1.04 (t, J=6.8 Hz, 3H), 2.90 (br q, J=6.8 Hz, 2H), 3.57 (s, 3H), 3.88 (d, J=5.5 Hz, 2H), 4.57 (s, 2H), 5.51 (s, 2H), 6.59 (d, J=5.6 Hz, 1H), 7.01–7.08 (m 4H), 7.19–7.30 (m, 3H), 7.55 (s, 1H), 7.99 (s, 1H), 8.40 (t, J=5.5 Hz, 1H).

B. Preparation of N-[2-[[3-(Aminooxoacetyl)-2-ethyl-1-(phenylmethyl)-1H-indol-4-yl]oxy]acetyl]glycine

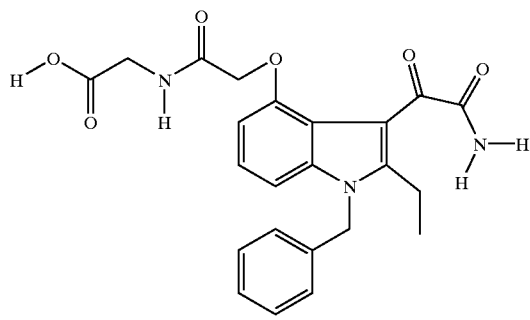

3a

To a solution of 2a (0.035 g, 0.078 mmol) in 1 mL THF, 1 mL MeOH and 0.25 mL distilled $H_2O$ was added 4.17N LiOH (0.093 mL, 0.388 mmol) at room temperature. After 2 hrs. the reaction mixture was acidified with 5N HCl (0.093 mL, 0.465 mmol) and concentrated in vacuo. The residue was taken up in $CH_2Cl_2$ then rapidly triturated with hexanes to give a yellow suspension which was filtered and dried in an 80° C. vacuum oven to give 0.0336 g of 3a as a yellow solid in 99% yield. $^1$H NMR (DMSO-$d_6$) δ 1.04 (t, J=5.9 Hz, 3H), 2.90 (br q, J=5.9 Hz, 2H), 3.80 (d, J=4.8 Hz, 2H), 4.56 (s, 2H), 5.51 (s, 2H), 6.62 (d, J=5.8 Hz, 1H), 7.01–7.28 (m, 7H), 7.54 (s, 1H), 7.99 (s, 1H), 8.31 (t, J=4.8 Hz, 1H), 12.25–12.75 (br s, 1H).

EXAMPLE 4

N-[2-[[3-(Aminooxoacetyl)-2-ethyl-1-(phenylmethyl)-1H-indol-4-yl]oxy]acetyl]-L-alanine

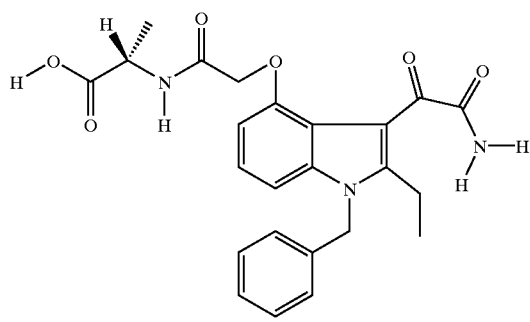

3b

A. Preparation of N-[2-[[3-(Aminooxoacetyl)-2-ethyl-1-(phenylmethyl)-1H-indol-4-yl]oxy]acetyl]-L-alanine Methyl Ester

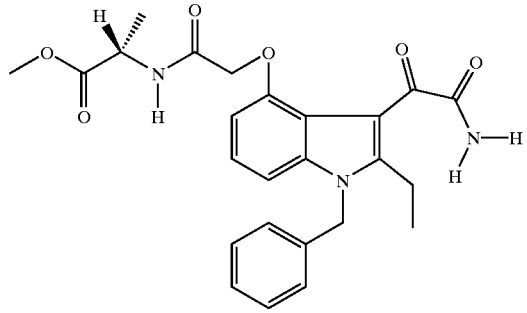

2b

Following the experimental procedure as described for 2a, 2b was obtained as a yellow solid in 65% yield. $^1$H NMR (DMSO-$d_6$) δ 1.04 (t, J=7.2 Hz, 3H), 1.29 (d, J=7.3 Hz, 3H), 2.91 (br q, J=7.2 Hz, 2H), 3.54 (s, 3H), 4.29 (qd, J 7.3, 6.8 Hz, 1H), 4.55 (s, 2H), 5.51 (s, 2H), 6.57 (m, 1H), 6.99 (d, J=7.4 Hz, 2H), 7.07–7.08 (m, 2H), 7.21–7.31 (m, 3H), 7.56 (s, 1H), 8.05 (s, 1H), 8.40 (d, J=6.8 Hz, 1H).

B. Preparation of N-[2-[[3-(Aminooxoacetyl)-2-ethyl-1-(phenylmethyl)-1H-indol-4-yl]oxy]acetyl]-L-alanine

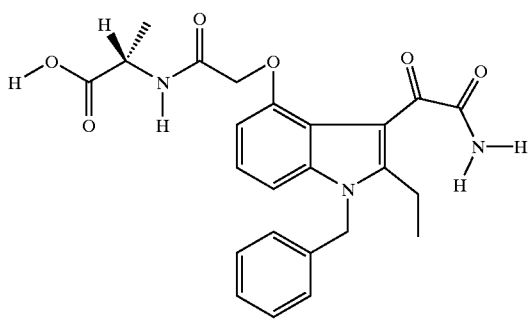

3b

Following the experimental procedure as described for preparing compound 3a, compound 3b, was obtained as a yellow solid in 89% yield. H NMR (DMSO-$d_6$) δ 1.04 (t, J=7.2 Hz, 3H), 1.29 (d, J=7.3 Hz, 3H), 2.91 (br q, J=7.2 Hz, 2H), 4.22 (td, J=7.2, 7.1 Hz, 1H), 4.54 (s, 2H), 5.51 (s, 2H), 6.60 (d, J=6.3 Hz, 1H), 7.00–7.09 (m, 4H), 7.21–7.30 (m, 3H), 7.53 (s, 1H), 8.03 (s, 1H), 8.31 (d, J=7.1 Hz, 1H), 12.75–12.84 (br s, 1H).

EXAMPLE 5

N-[2-[[3-(Aminooxoacetyl)-2-ethyl-1-(phenylmethyl)-1H-indol-4-yl]oxy]acetyl]-L-leucine

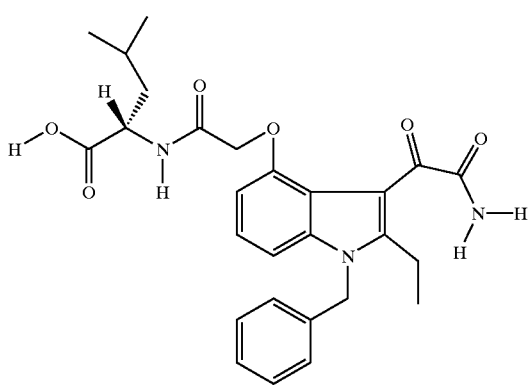

3c

A. Preparation of N-[2-[[3-(Aminooxoacetyl)-2-ethyl-1-(phenylmethyl)-1H-indol-4-yl]oxy]acetyl]-L-leucine Methyl Ester

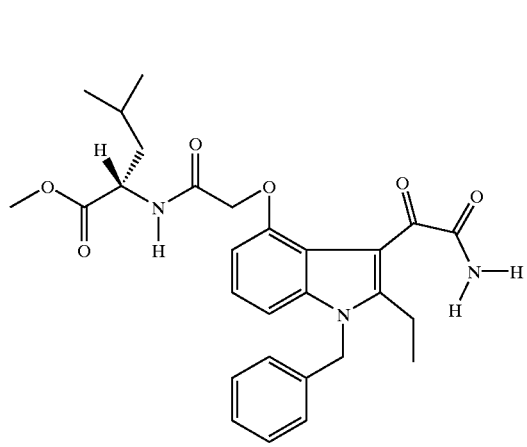

2c

Following the experimental procedure as described for 2a, 2c was obtained as a yellow solid in 98% yield. $^1$H NMR (DMSO-d$_6$) δ 0.67 (d, J=5.5 Hz, 3H), 0.72 (d, J=5.7 Hz, 3H), 1.05 (t, J=7.2 Hz, 3H), 1.30–1.50 (m, 2H), 1.51–1.64 (m, 1H), 2.91 (br q, J=7.2 Hz, 2H), 3.55 (s, 3H), 4.20–4.27 (m, 1H), 4.57 (s, 2H), 5.52 (s, 2H), 6.53–6.56 (m, 1H), 6.97–7.08 (m, 4H), 7.21–7.29 (m, 3H), 7.56 (s, 1H), 8.07 (s, 1H), 8.37 (d, J=7.3 Hz, 1H).

B. Preparation of N-[2-[[3-(Aminooxoacetyl)-2-ethyl-1-(phenylmethyl)-1H-indol-4-yl]oxy]acetyl]-L-leucine

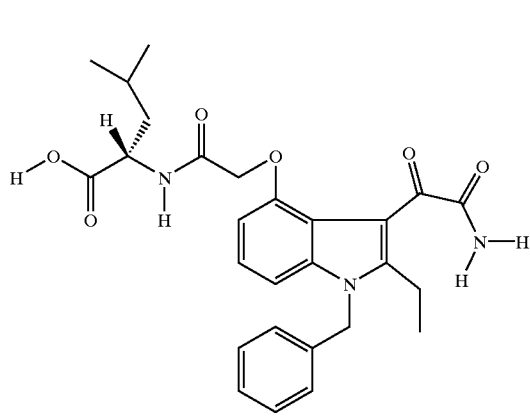

3c

Following the experimental procedure as described for 3a, 3c was obtained as a yellow solid in 75% yield. $^1$H NMR (DMSO-d$_6$) δ 0.76 (d, J=5.7 Hz, 3H), 0.78 (d, J=6.1 Hz, 3H), 1.21 (t, J=7.3 Hz, 3H), 1.39–1.43 (m, 1H), 1.69 (t, J=7.3 Hz, 2H), 2.96 (br q, J=7.3 Hz, 2H), 4.57–4.65 (m, 1H), 4.69 (d, J=16.0 Hz, 1H), 4.78 (d, J=16.0 Hz, 1H), 5.38 (s, 2H), 6.59 (d, J=8.0 Hz, 1H), 6.89 (d, J=8.2 Hz, 1H), 6.95–7.12 (m, 5H), 7.26–7.32 (m, 3H), 8.17 (d, J=8.2 Hz, 1H).

EXAMPLE 6

N-[2-[[3-(Aminooxoacetyl)-2-ethyl-1-(phenylmethyl)-1H-indol-4-yl]oxy]acetyl]-L-aspartic Acid

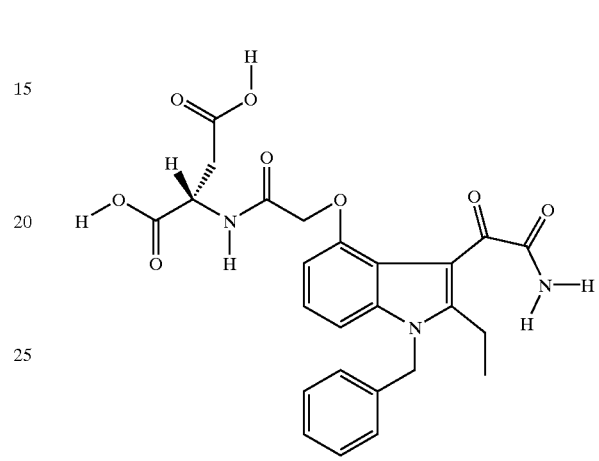

3d

A. Preparation of N-[2-[[3-(Aminooxoacetyl)-2-ethyl-1-(phenylmethyl)-1H-indol-4-yl]oxy]acetyl]-L-aspartic Acid Dimethyl Ester

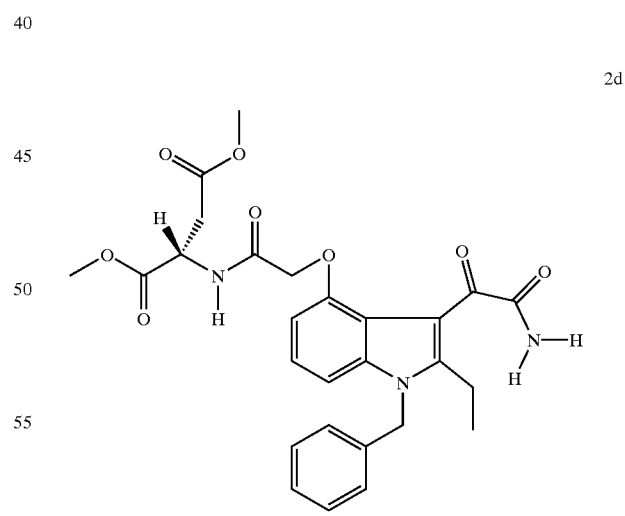

2d

Following the experimental procedure as described for 2a, 2d was obtained as a yellow solid in 88% yield. $^1$H NMR (DMSO-d$_6$) δ 1.04 (t, J=7.3 Hz, 3H), 2.72 (dd, J=16.6–7.1 Hz, 1H), 2.83 (dd, J=16.7, 7.1 Hz, 1H), 2.90 (br q, J=7.3 Hz, 2H), 3.49 (s, 3H), 3.55 (s, 3H), 4.54 (s, 2H), 4.66 (m, 1H), 5.51 (s, 2H), 6.54 (m, 1H), 6.97–7.09 (m, 4H), 7.21–7.30 (m, 3H), 7.50 (s, 1H), 7.97 (s, 1H), 8.52 (d, J=7.9 Hz, 1H).

B. Preparation of N-[2-[[3-(Aminooxoacetyl)-2-ethyl-1-(phenylmethyl)-1H-indol-4-yl]oxy]acetyl]-L-aspartic Acid

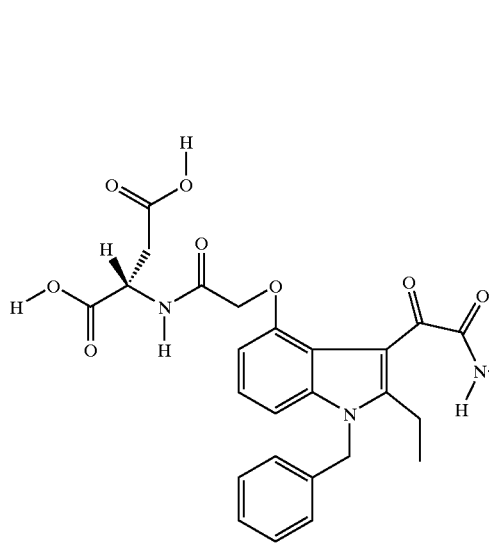

3d

Following the experimental procedure as described for 3a, 3d was obtained as a yellow solid in 99% yield. $^1$H NMR (DMSO-d$_6$) δ 1.04 (t, J=7.2 Hz, 3H), 2.52–2.76 (m, 2H), 2.90 (br q, J=7.2 Hz, 2H), 4.53 (s, 2H), 4.53–4.60 (m, 1H), 5.50 (s, 2H), 6.59 (d, J=7.2 Hz, 1H), 6.98–7.09 (m, 4H), 7.19–7.30 (m, 3H), 7.47 (s, 1H), 7.94 (s, 1H), 8.33 (d, j=7.8 Hz, 1H), 12.40–13.20 (br s, 2H).

EXAMPLE 7

N-[2-[[3-(Aminooxoacetyl)-2-ethyl-1-(phenylmethyl)-1H-indol-4-yl]oxy]acetyl]-L-phenylalanine

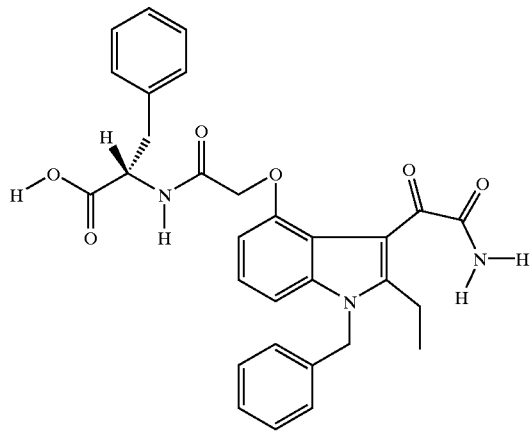

3e

A. Preparation of N-[2-[[3-(Aminooxoacetyl)-2-ethyl-1-(phenylmethyl)-1H-indol-4-yl]oxy]acetyl]-L-phenylalanine Methyl Ester

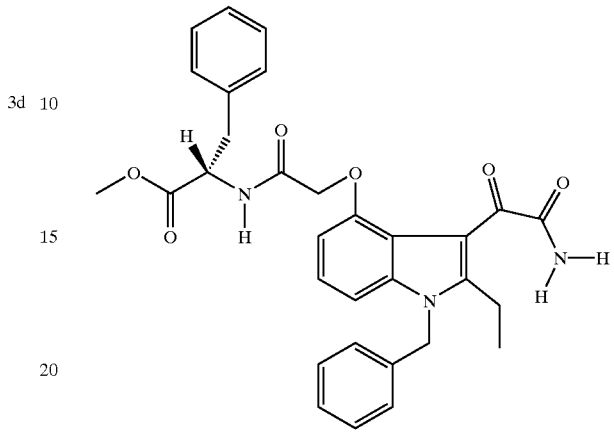

2e

Following the experimental procedure as described for 2a, 2e was obtained as a yellow solid in 68% yield. $^1$H NMR (DMSO-d$_6$) δ 1.06 (t, J=7.2 Hz, 3H), 2.88–3.03 (m, 4H), 3.54 (s, 3H), 4.47–4.50 (m, 1H), 4.50 (s, 2H), 5.52 (s, 2H), 6.41 (d, J=7.7 Hz, 1H), 6.98–7.11 (m, 9H), 7.21–7.30 (m, 3H), 7.47 (s, 1H), 8.06 (s, 1H), 8.52 (d, J=7.7 Hz, 1H).

B. Preparation of N-[2-([3-(Aminooxoacetyl)-2-ethyl-1-(phenylmethyl)-1H-indol-4-yl]oxyylacetyl]-L-phenylalanine

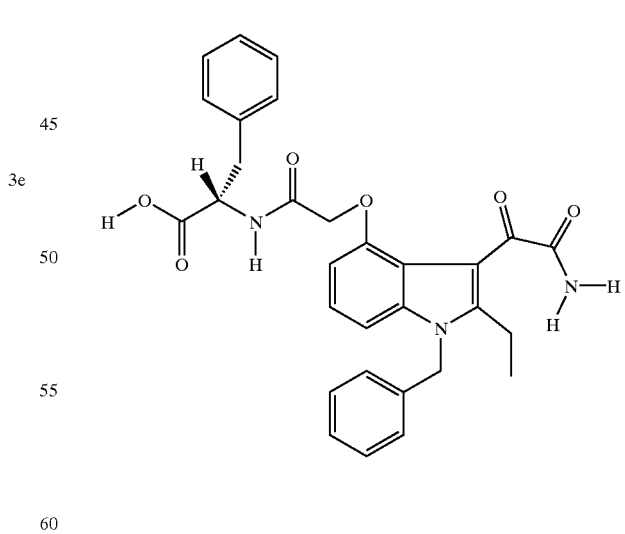

3e

Following the experimental procedure as described for 3a, 3e was obtained as a yellow solid in 93% yield. $^1$H NMR (DMSO-d$_6$) δ 1.04 (t, J=7.1 Hz, 3H), 2.85–3.12 (m, 4H), 4.17–4.26 (m, 1H), 4.54 (s, 2H), 5.51 (s, 2H), 6.59 (d, J=6.4

Hz, 1H), 6.98–7.09 (m, 9H), 7.19–7.30 (m, 3H), 7.53 (s, 1H), 8.03 (s, 1H), 8.30 (d, J=7.0 Hz, 1H), 12.50 (br s, 1H).

EXAMPLE 8

[2-[[3-(Aminooxoacetyl)-2-ethyl-1-(phenylmethyl)-1H-indol-4-yl]oxy]acetamido]malonic Acid

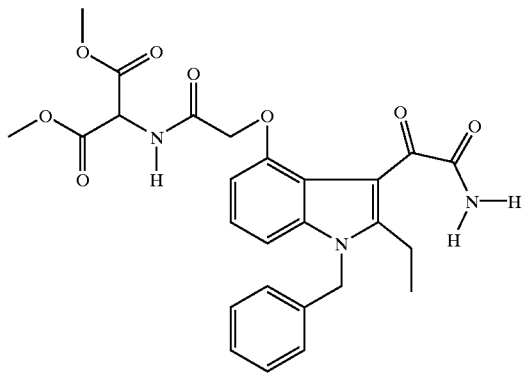

3f

A. Preparation of [2-[[3-(Aminooxoacetyl)-2-ethyl-1-(phenylmethyl)-1H-indol-4-yl]oxy]acetamido]malonic Acid Dimethyl Ester

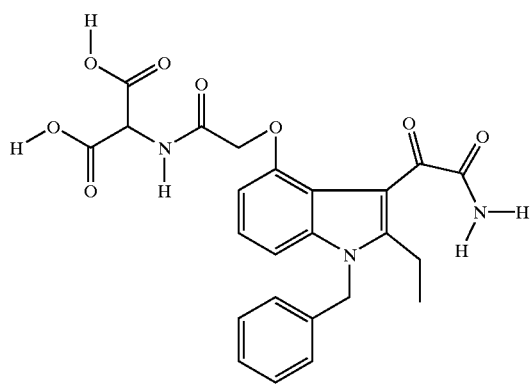

2f

Following the experimental procedure as described for 2a, 2f was obtained as a yellow solid in 98% yield. $^1$H NMR (DMSO-$d_6$) δ 1.04 (t, J=7.3 Hz, 3H), 2.90 (br q, J=7.3 Hz, 2H), 3.64 (s, 6H), 4.63 (s, 2H), 5.16 (d, J=7.1 Hz, 1H), 5.51 (s, 2H), 6.54–6.56 (m, 1H), 6.98–7.09 (m, 4H), 7.21–7.30 (m, 3H), 7.43 (s, 1H), 7.88 (s, 1H), 8.90 (d, J=7.2 Hz, 1H).

B. Preparation of [2-[[3-(Aminooxoacetyl)-2-ethyl-1-(phenylmethyl)-1H-indol-4-yl]oxy]acetamido]malonic Acid

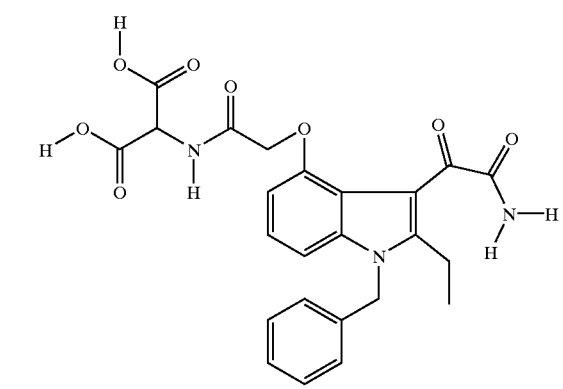

3f

Following the experimental procedure as described for 3a, 3f was obtained as a yellow solid in 99% yield. $^1$H NMR (DMSO-$d_6$) δ 8 1.04 (t, J=6.9 Hz, 3H), 2.89 (br q, J=7.3 Hz, 2H), 4.62 (s, 2H), 4.91 (d, J=7.2 Hz, 1H), 5.50 (s, 2H), 6.57 (d, J=7.2 Hz, 1H), 6.98–7.09 (m, 4H), 7.18–7.30 (m, 3H), 7.37 (s, 1H), 7.83 (s, 1H), 8.55 (d, J=7.2 Hz, 1H), 12.30–13.00 (br s, 2H).

EXAMPLE 9

N-[2-[[3-(Aminooxoacetyl)-2-ethyl-1-(phenylmethyl)-1H-indol-4-yl]oxy]acetyl]-L-valine

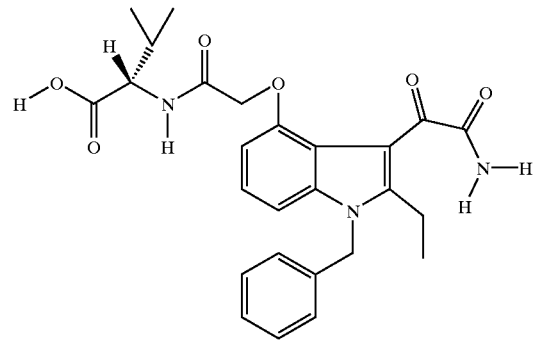

3g

A. Preparation of N-[2-[[3-(Aminooxoacetyl)-2-ethyl-1-(phenylmethyl)-1H-indol-4-yl]oxy]acetyl]-L-valine Methyl Ester

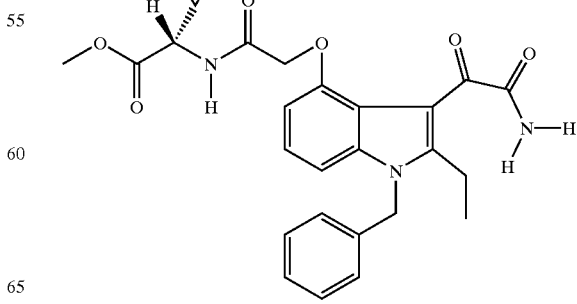

2g

Following the experimental procedure as described for 2a, 2g was obtained as a yellow solid in 96% yield. $^1$H NMR (DMSO-$d_6$) δ 0.71 (d, J=6.8 Hz, 3H), 0.74 (d, J=7.0 Hz, 3H), 1.05 (t, J=7.2 Hz 3H), 1.99–2.05 (m, 1H), 2.90 (br q, J=7.2 Hz, 2H), 3.54 (s, 3H), 4.11 (br t, J=7.0 Hz, 1H), 4.60 (s, 2H), 5.52 (s, 2H), 6.52 (d, J=4.4 Hz, 1H), 6.95 (d, J=7.2 Hz, 2H), 7.06 (br s, 2H), 7.18–7.29 (m, 3H), 7.52 (s, 1H), 8.04 (s, 1H), 8.20 (d, J=7.8 Hz, 1H)

B. Preparation of N-[2-[[3-(Aminooxoacetyl)-2-ethyl-1-(phenylmethyl)-1H-indol-4-yl]oxy]acetyl]-L-valine

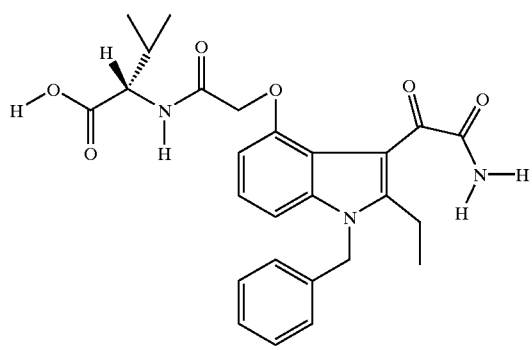

3g

Following the experimental procedure as described for 3a, 3g was obtained as a yellow solid in 94% yield. $^1$H NMR (DMSO-$d_6$) δ 0.71 (d, J=6.9 Hz, 3H), 0.75 (d, J=6.8 Hz, 3H), 1.04 (t, J=7.3 Hz 3H), 2.01–2.07 (m, 1H), 2.90 (br q, J=7.3 Hz, 2H), 4.09 (br dd, J=7.9, 6.2 Hz, 1H), 4.60 (s, 2H), 5.51 (s, 2H), 6.54 (d, J=6.1 Hz, 1H), 6.95 (d, J=7.3 Hz, 2H), 6.99–7.08 (m, 2H), 7.18–7.29. (m, 3H), 7.49 (s, 1H), 8.01 (s, 1H), 8.08 (d, J=8.2 Hz, 1H), 12.63 (br s, 1H)

EXAMPLE 10

N-[2-[[3-(Aminooxoacetyl)-2-ethyl-1-(phenylmethyl)-1H-indol-4-yl]oxy]acetyl]-L-isoleucine 3h

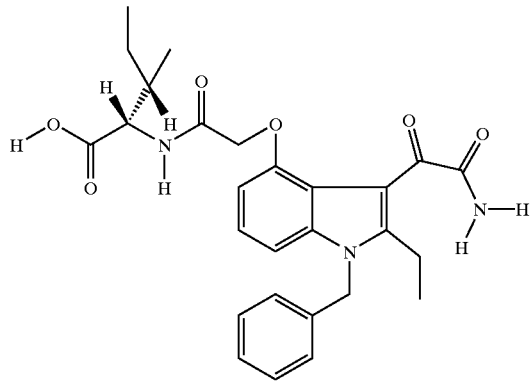

A. Preparation of N-[2-[[3-(Aminooxoacetyl)-2-ethyl-1-(phenylmethyl)-1H-indol-4-yl]oxy]acetyl]-L-isoleucine Methyl Ester

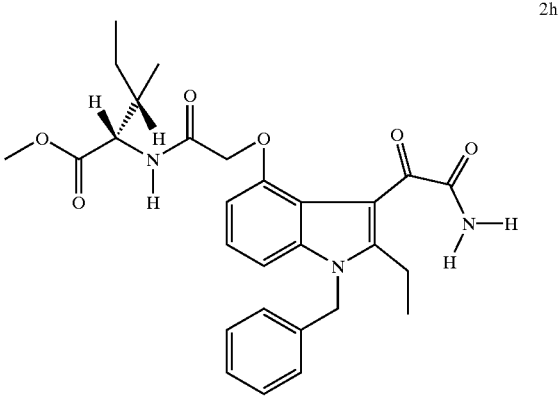

2h

Following the experimental procedure as described for 2a, 2h was obtained as a yellow solid in 73% yield. $^1$H NMR (DMSO-$d_6$) δ 0.64–0.71 (m, 6H), 0.99–1.08 (m, 4H), 1.21–1.26 (m, 1H), 1.76–1.80 (m, 1H), 2.91 (br q, J=7.4 Hz, 2H), 3.53 (s, 3H), 4.15 (br t, J=7.2 Hz, 1H), 4.60 (s, 2H), 5.52 (s, 2H), 6.52 (m, 1H), 6.96 (d, J=7.2 Hz, 2H), 7.02–7.07 (m, 2H), 7.18–7.29 (m, 3H), 7.53 (s, 1H), 8.04 (s, 1H), 8.23 (d, J=7.7 Hz, 1H).

B. Preparation of N-[2-[[3-(Aminooxoacetyl)-2-ethyl-1-(phenylmethyl)-1H-indol-4-yl]oxy]acetyl]-L-isoleucine

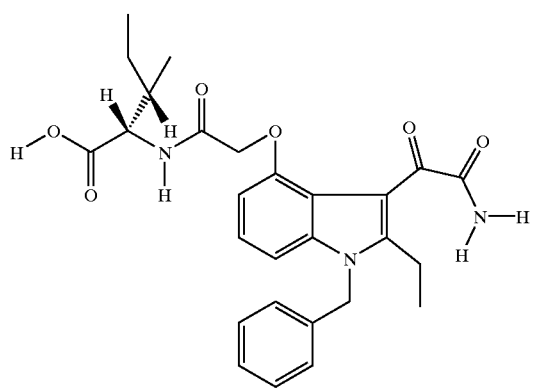

3h

Following the experimental procedure as described for 3a, 3h was obtained as a yellow solid in 92% yield. $^1$H NMR (DMSO-$d_6$) δ 0.64–0.84 (m, 6H), 1.04 (t, J=7.2 Hz, 3H), 1.21–1.28 (m, 2H), 1.76–1.80 (m, 1H), 2.91 (br q, J=7.2 Hz, 2H), 4.12 (br t, J=7.3 Hz, 1H), 4.59 (s, 2H), 5.51 (s, 2H), 6.55 (d, J=6.4 Hz, 1H), 6.96 (d, J=7.2 Hz, 2H), 7.01–7.08 (m, 2H), 7.21–7.29 (m, 3H), 7.51 (s, 1H), 8.01 (s, 1H), 8.11 (d, J=7.4 Hz, 1H), 12.40–12.65 (br s, 1H).

ASSAY

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

Reagents:
  REACTION BUFFER —$CaCl_2 \cdot 2H_2O$ (1.47 g/L) KCl (7.455 g/L) Bovine Serum Albumin (fatty acid free) (1 g/L) (Sigma A-7030, product of Sigma Chemical Co., St. Louis Mo., USA) TRIS HCl (3.94 g/L) pH 7.5 (adjust with NaOH)
  ENZYME BUFFER-0.05 $NaOAc.3H_2O$, pH 4.5 0.2 NaCl Adjust pH to 4.5 with acetic acid DTNB-5,5'-dithiobis-2-nitrobenzoic acid
  RACEMIC DIHEPTANOYL THIO-PC racemic 1,2-bis (heptanoylthio)-1,2-dideoxy-sn-glycero-3-phosphorylcholine TRITON X-100™ prepare at 6.249 mg/ml in reaction buffer to equal 10 uM.
  REACTION MIXTURE
    A measured volume of racemic diphetanoyl thio PC supplied in chloroform at a concentration of 100 mg/ml is taken to dryness and redissolved in 10 millimolar
    TRITON X-100™ nonionic detergent aqueous solution.
  Reaction Buffer is added to the solution, then DTNB to give the Reaction Mixture.
  The reaction mixture thus obtained contains 1 mM diheptanoly thio-PC substrate, 0.29 mm Triton X-$_{100}$™ detergent, and 0.12 mm DTMB in a buffered aqueous solution at pH 7.5.
Assay Procedure:
  1. Add 0.2 ml reaction mixture to all wells;
  2. Add 10 ul test compound (or solvent blank) to appropriate wells, mix 20 seconds;
  3. Add 50 nanograms of $sPLA_2$ (10 microliters) to appropriate wells;
  4. Incubate plate at 40° C. for 30 minutes;
  5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ were determined by plotting log concentration versus inhibition values in the range from 10–90% inhibition.

Results of Human Secreted Phospholipase $A_2$ Inhibition Tests

TABLE

| Compound No. from Examples 3–10 | Inhibition of human secreted $PLA_2$ IC50 ± mean deviation (3–4 tests) (nM) |
|---|---|
| 1 | 49 |
| 2A | 529 |
| 2B | 533 |
| 2C | 82 |
| 2D | 874 |
| 2E | 666 |
| 2F | 698 |
| 2G | 283 |
| 2H | 166 |
| 3A | 71 |
| 3B | 59 |
| 3C | 28 |
| 3D | 132 |
| 3E | 64 |
| 3F | 44.7 |
| 3G | 36.4 |
| 3H | 25.1 |

The compound of Example 1 is highly active in inhibiting $SPLA_2$.

While the present invention has been illustrated above by certain specific embodiments, it is not intended that these specific examples should limit the scope of the invention as described in the appended claims.

We claim:
1. An indole compound represented by the formula (II), or a pharmaceutically acceptable salt, solvate, or prodrug thereof;

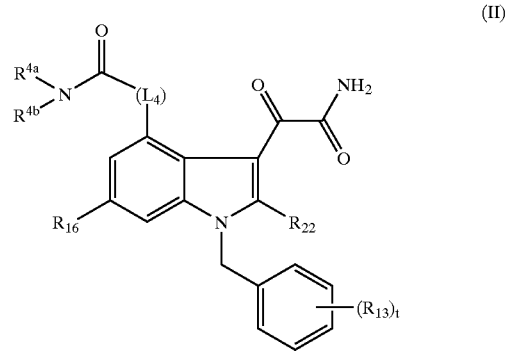

(II)

wherein
  $R_{22}$ is selected from hydrogen, methyl, ethyl, propyl, isopropyl, cyclopropyl, —F, —$CF_3$, —Cl, —Br, or —O—$CH_3$;
  $R^{4a}$ is hydrogen; and
  $NR^{4b}$ is an amino acid group with the nitrogen atom being part of the amino group of the amino acid, and —($L_4$)— is a divalent group selected from;

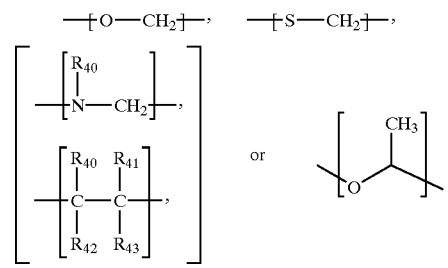

$R_{16}$ is selected from hydrogen, $C_1$–$C_8$ alkyl, $C_1$–$C_8$ alkoxy, $C_1$–$C_8$ alkylthio $C_1$–$C_8$ haloalkyl, $C_1$–$C_8$ hydroxyalkyl, and halo;

$R_{13}$ is selected from hydrogen and $C_1$–$C_8$ alkyl, $C_1$–$C_8$ alkoxy, —S—($C_1$–$C_8$ alkyl $C_1$–$C_8$ haloalkyl, $C_1$–$C_8$ hydroxyalkyl, phenyl, halophenyl, and halo, and t is an integer from 0 to 5.

2. A pharmaceutical formulation comprising a indole compound as claimed in claim 1 together with a pharmaceutically acceptable carrier or diluent therefor.

3. A method of therapeutically reducing the release of sPLA$_2$ initiated fatty acids to treat inflammatory diseases which comprises contacting sPLA$_2$ with a therapeutically effective amount of an indole compound of formula I.

4. A compound selected from the group consisting of:

N-[2-[[3-(Aminooxoacetyl)-2-ethyl-1-(phenylmethyl)-1H-indol-4-yl]oxy]acetyl]glycine;

N-[2-[[3-(Aminooxoacetyl)-2-ethyl-1-(phenylmethyl)-1H-indol-4-yl]oxy]acetyl]glycine methyl ester;

N-[2-[[3-(Aminooxoacetyl)-2-ethyl-1-(phenylmethyl)-1H-indol-4-yl]oxy]acetyl]-L-alanine;

N-[2-[[3-(Aminooxoacetyl)-2-ethyl-1-(phenylmethyl)-1H-indol-4-yl]oxy]acetyl]-L-alanine methyl ester;

N-[2-[[3-(Aminooxoacetyl)-2-ethyl-1-(phenylmethyl)-1H-indol-4-yl]oxy]acetyl]-L-leucine;

N-[2-[[3-(Aminooxoacetyl)-2-ethyl-1-(phenylmethyl)-1H-indol-4-yl]oxy]acetyl]-L-leucine methyl ester;

N-[2-[[3-(Aminooxoacetyl)-2-ethyl-1-(phenylmethyl)-1H-indol-4-yl]oxy]acetyl]-L-aspartic acid;

N-[2-[[3-(Aminooxoacetyl)-2-ethyl-1-(phenylmethyl)-1H-indol-4-yl]oxy]acetyl]-L-aspartic acid dimethyl ester;

-N-[2-[[3-(Aminooxoacetyl)-2-ethyl-1-(phenylmethyl)-1H-indol-4-yl]oxy]acetyl]-L-phenylalanine;

N-[2-[[3-(Aminooxoacetyl)-2-ethyl-1-(phenylmethyl)-1H-indol-4-yl]oxy]acetyl]-L-phenylalanine methyl ester;

N-[2-[[3-(Aminooxoacetyl)-2-ethyl-1-(phenylmethyl)-1H-indol-4-yl]oxy]acetamido]malonic acid;

[2-[[3-(Aminooxoacetyl)-2-ethyl-1-(phenylmethyl)-1H-indol-4-yl]oxy]acetamido]malonic acid dimethyl ester;

N-[2-[[3-(Aminooxoacetyl)-2-ethyl-1-(phenylmethyl)-1H-indol-4-yl]oxy]acetyl]-L-valine;

N-[2-[[3-(Aminooxoacetyl)-2-ethyl-1-(phenylmethyl)-1H-indol-4-yl]oxy]acetyl]-L-valine methyl ester;

N-[2-[[3-(Aminooxoacetyl)-2-ethyl-1-(phenylmethyl)-1H-indol-4-yl]oxy]acetyl]-L-isoleucine;

N-[2-[[3-(Aminooxoacetyl)-2-ethyl-1-(phenylmethyl)-1H-indol-4-yl]oxy]acetyl]-L-isoleucine methyl ester.

5. A method of treating a mammal to alleviate the pathological effects of Inflammatory Diseases comprising administering to said mammal a therapeutically effective amount of a compound according to claim 4.

6. A formulation containing a therapeutically effective amount of the compound of claim 4 for the treatment of Inflammatory Diseases.

* * * * *